US008849576B2

(12) United States Patent
Amri et al.

(10) Patent No.: US 8,849,576 B2
(45) Date of Patent: Sep. 30, 2014

(54) PHYLOGENETIC ANALYSIS OF MASS SPECTROMETRY OR GENE ARRAY DATA FOR THE DIAGNOSIS OF PHYSIOLOGICAL CONDITIONS

(76) Inventors: Hakima Amri, Bethesda, MD (US); Mones Abu-asab, Bethesda, MD (US); Mohamed Chaouchi, Bethesda, MD (US)

(*) Notice: Subject to any disclaimer, the term of this patent is extended or adjusted under 35 U.S.C. 154(b) by 1683 days.

(21) Appl. No.: 11/740,994

(22) Filed: Apr. 27, 2007

(65) Prior Publication Data
US 2007/0259363 A1    Nov. 8, 2007

Related U.S. Application Data

(60) Provisional application No. 60/796,351, filed on Apr. 28, 2006.

(51) Int. Cl.
| | |
|---|---|
| G01N 33/48 | (2006.01) |
| G01N 31/00 | (2006.01) |
| G06F 19/24 | (2011.01) |
| G06F 19/00 | (2011.01) |
| G06F 19/14 | (2011.01) |
| G06F 19/20 | (2011.01) |

(52) U.S. Cl.
CPC ............ *G06F 19/24* (2013.01); *G06F 19/3437* (2013.01); *G06F 19/14* (2013.01); *G06F 19/20* (2013.01)
USPC .............................................. 702/19; 702/22

(58) Field of Classification Search
None
See application file for complete search history.

(56) References Cited

U.S. PATENT DOCUMENTS

| | | | | |
|---|---|---|---|---|
| 5,769,074 | A * | 6/1998 | Barnhill et al. ............... | 600/300 |
| 2003/0225771 | A1* | 12/2003 | Mossel ......................... | 707/100 |
| 2004/0126813 | A1* | 7/2004 | Debe et al. .................... | 435/7.1 |
| 2004/0219565 | A1* | 11/2004 | Kauppinen et al. .............. | 435/6 |

OTHER PUBLICATIONS

Bernard et al. Identification and assessment of known and novel human papillomaviruses by polymerase chain reaction amplification, restriction fragment length polymorphisms, nucleotide sequence, and phylogenetic algorithms. The Journal of Infectious Diseases, 1994, vol. 170, pp. 1077-1085.*

Zapata et al. A Diverse family of proteins containing tumor necrosis factor receptor-associated factor domains. The Journal of Biological Chemistry, 2001, vol. 276, pp. 24242-24252.*

(Continued)

*Primary Examiner* — Russell S Negin
(74) *Attorney, Agent, or Firm* — Merek, Blackmon & Voorhees, LLC

(57) ABSTRACT

A universal data-mining platform is provided capable of analyzing mass spectrometry (MS) serum proteomic profiles and/or gene array data to produce biologically meaningful classification; i.e., group together biologically related specimens into clades. This platform utilizes the principles of phylogenetics, such as parsimony, to reveal susceptibility to cancer development (or other physiological or pathophysiological conditions), diagnosis and typing of cancer, identifying stages of cancer, as well as post-treatment evaluation. By outgroup comparison, the parsing algorithm identifies under and/or overexpressed gene values or in the case of sera, (i) novel or (ii) vanished MS peaks, and peaks signifying (iii) up or (iv) down regulated proteins, and scores the variations as either derived (do not exist in the outgroup set) or ancestral (exist in the outgroup set); the derived is given a score of "1", and the ancestral a score of "0"—these are called the polarized values.

23 Claims, 7 Drawing Sheets

(56) References Cited

OTHER PUBLICATIONS

Sauter et al. Proteomic analysis of nipple aspirate fluid using SELDI-TOF-MS. International Journal of Cancer, vol. 114, pp. 791-796, posted online on Dec. 17, 2004.*

Proof that Sauter et al. was published online on Dec. 17, 2004, obtained online on Jan. 8, 2010 << http://www3.interscience.wiley.com >> 1 page.*

Antonnson et al. Healthy skin of many animal species harbors papillomaviruses which are closely related to their human counterparts. Journal of Virology, 2002, vol. 76, pp. 12537-12542.*

Proikas-Cezanne et al. WIPI-1a (WIPI49), a member of the novel 7-bladed WIPI protein family, is aberrantly expressed in human cancer and is linked to starvation-induced autophagy. Oncogene, 2004, vol. 23, pp. 9314-9325.*

Zhu et al. Detection of cancer-specific markers amid massive mass spectral data. PNAS, 2003, vol. 100, pp. 14666-14671.*

Golub et al. Molecular classification of cancer: class discovery and class prediction by gene expression monitoring. Science, 1999, vol. 286, pp. 531-537.*

Li et al. Proteomics and bioinformatics approaches for identification of serum biomarkers to detect breast cancer. Clinical Chemistry, vol. 48, 2002, pp. 1296-1304.*

Van Ranst et al. Phylogenetic classification of human papillomaviruses: correlation with clinical manifestations. Journal of General Virology, vol. 73, 1992, pp. 2653-2660.*

Beillard et al. Evaluation of candidate control genes for diagnosis and residual disease detection in leukemic patients using 'real-time' quantitative reverse-transcriptase polymerase chain reaction (RQ-PCR)—a Europe against cancer program. Leukemia, vol. 17, 2003, pp. 2474-2486.*

Bomprezzi et al. Gene expression profile in multiple sclerosis patients and healthy controls: identifying pathways relevant to disease. Human Molecular Genetics, 2003, vol. 12, pp. 2191-2199.*

Planet et al. Systematic analysis of DNA microarray data: ordering and interpreting patterns of gene expression. Genome Research, 2001, vol. 11, pp. 1149-1155.*

* cited by examiner

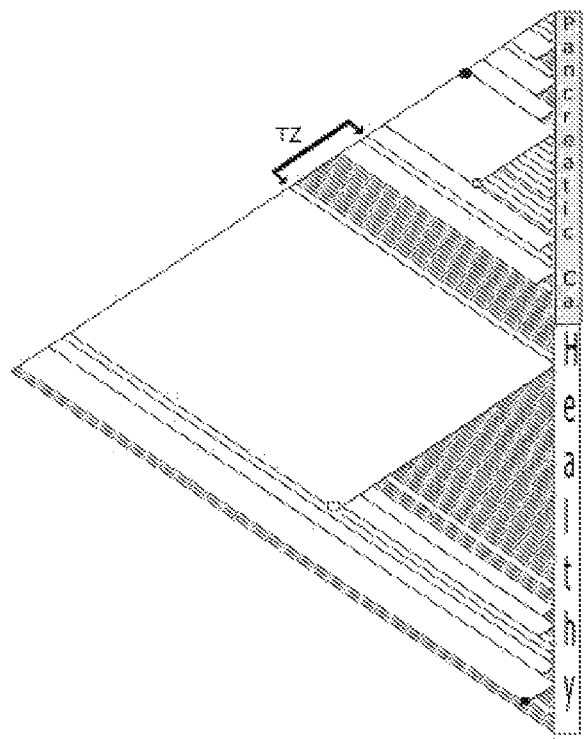
Figure 2.A
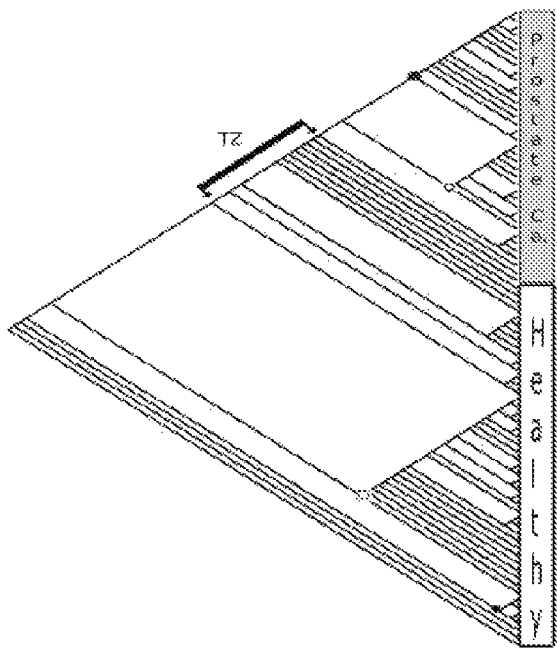
Figure 2.B

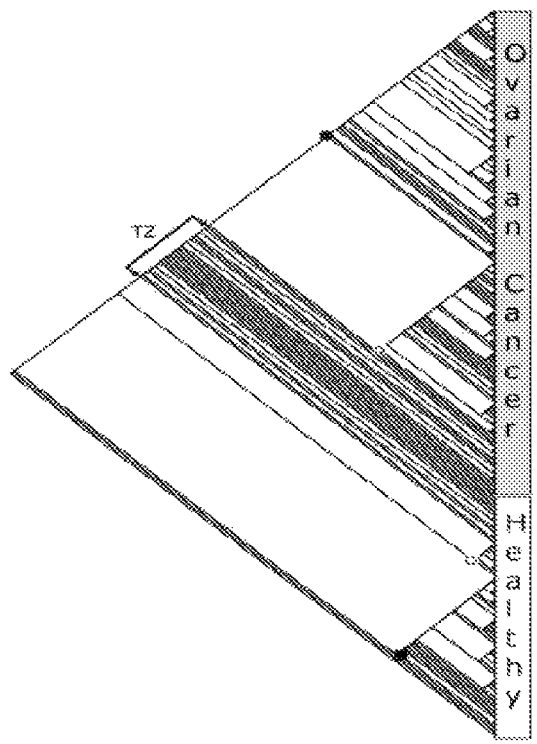
Figure 2.C
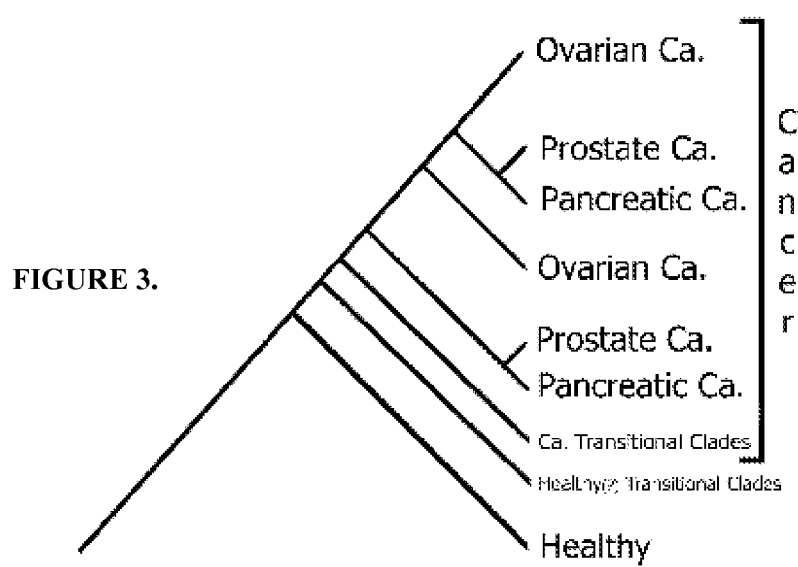
FIGURE 3.

PHYLOGENETIC ANALYSIS OF MASS SPECTROMETRY OR GENE ARRAY DATA FOR THE DIAGNOSIS OF PHYSIOLOGICAL CONDITIONS

CROSS REFERENCE TO RELATED APPLICATIONS

This application claims the benefit of U.S. Provisional Application 60/796,351, filed Apr. 28, 2006, which is incorporated herein by reference.

BACKGROUND OF THE INVENTION

1. Field of the Invention

The present invention relates a universal data-mining platform capable of analyzing mass spectrometry (MS) serum proteomic profiles and/or gene array data to produce biologically meaningful classification; i.e., group together biologically related specimens. This platform utilizes the principles of phylogenetics, such as parsimony, to analyze the genetic, physiological, and developmental processes where deviation from the normal conditions of the population need to be assessed, profiled, or defined as well as assessing the normal physiological pathways. This may be used, for example, to reveal susceptibility to cancer development, diagnosis and typing of cancer, identifying stages of cancer, as well as post-treatment evaluation. Furthermore, the uniquely derived characters that it identifies are potential biomarkers for cancers and their subclasses.

2. Description of the Prior Art

Classifying specimens on the basis of their overall similarity (e.g., phenetic approaches such as clustering) is problematic. Comparability of proteomic analyses performed in diverse locations is unattainable due to the lack of broadly acceptable universal methods of analysis. Further, the use of mass spectrometry (MS) of serum proteins to produce clinically useful profiles has proven to be challenging, and has generated some controversy. Although several methods have been published thus far, they all have either had cancer type-specific sorting algorithms that produced below 95% specificity and did not apply well across other cancer types, did not utilize all potentially useful variability within the data, or were not widely tested. Furthermore, their relative success has been limited to diagnoses without any predictive conclusions. Since cancer is an evolutionary condition produced by a set of mutations, the present invention applies analysis that includes evolutionary sound methods of analysis.

SUMMARY OF THE INVENTION

The current invention introduces a repeatable, phylogenetic analysis that we termed phyloproteomics and phyloarray analyses, namely, universal evolutionary approaches to the analysis of MS serum data and/or gene expression data that produces biologically meaningful groupings of specimens, permits comparability among analyses, and demonstrates that its groupings have a high clinical relevance. It should be noted throughout the application that while either MS serum data or gene expression data can be analyzed to group specimens into particular clades, the specimens are analyzed separately depending on the analytical method involved, i.e., serum to serum or gene expression to gene expression.

Phyloproteomics is based on the postulation that specimens sharing uniquely derived protein(s) (synapomorphies) belong to an evolutionary unique group called a clade. Phyloarray, likewise, is a phylogenetic approach that offers an alternative to gene-listing, statistical gene-linkage, and clustering, and produces a biologically meaningful classification of specimens through hierarchical class discovery. Phyloarray is a postulation that specimens sharing unique shared derived gene value (synapomorphies) belong to their own evolutionary clade. To place specimens into their corresponding clade(s), the invention utilizes two algorithms: a new data-mining parsing algorithm created by the Applicants (UNIPAL/E-UNIPAL) as explained below, and a publicly available phylogenetic algorithm (MIX). By outgroup comparison (i.e., using a normal set as the standard reference), the parsing algorithm identifies under and/or overexpressed gene values or in the case of sera, (i) novel or (ii) vanished MS peaks, and peaks signifying (iii) up or (iv) down regulated proteins, and scores the variations as either derived (do not exit in the outgroup set) or ancestral (exist in the outgroup set); the derived is given a score of "1", and the ancestral a score of "0"—these are called the polarized values. The polarity assessment process does not reduce the data size, but rather polarized each value into ancestral or derived. The phylogenetic parsimony algorithm uses these scores to produce the most parsimonious phylogenetic classification of the specimens. This is a new approach that doesn't rely on pattern recognition, but rather on the shared derived gene values or MS derived values of the particular specimen. To characterize a specimen for diagnosis, the gene or MS profile of a specimen has to be compared to that of a large group of normal specimens. This comparison reveals the derived gene value and/or four types of accumulated derived differences in sera mentioned above. It is these derived states that determine the place of the specimen in a phylogenetic classification. The number of differences between an unhealthy (e.g., "diseased") specimen and normal ones, as we have determined, can be in the hundreds, and therefore, it is very simplistic to think that a small number of genes' means and folds or protein peaks can be sufficient to characterize a specimen and diagnose a cancer. Our approach utilizes all information obtainable from micro array or mass spectra analysis to characterize a specimen. In addition, it permits the comparison between data sets obtained from different MS machines; by carrying the outgroup comparison on each data set separately, each classification can be compared to the others produced by different machines and laboratories. In the same way, it facilitates interplatform comparability of gene expression data even when produced by different platforms and laboratories.

None of the prior art, taken either singly or in combination, is seen to describe the instant invention as claimed.

It is therefore an object of the invention to classify tissue in the spectrum of healthy to unhealthy (e.g., "cancerous") using a phylogenic analysis of the specimen data using a universal data-mining parsing algorithm (e.g., UNIPAL/E-UNIPAL) to analyze the evolutionary progress of tissue from healthy to adulterated (e.g., "cancerous") states.

It is another object to develop qualitative and quantitative universal data-mining parsing algorithm (UNIPAL/E-UNIPAL) that can be used for sorting out MS cancer serum proteomic data and gene-expression microarray into derived and ancestral states (apomorphic and plesiomorphic) by outgroup comparison (polarity assessment) to an outgroup of non-diseased specimens.

It is another object of the invention to use a universal data-mining parsing algorithm (UNIPAL/E-UNIPAL) to sort out MS cancer serum proteomic data and gene-expression microarray into derived and ancestral states (apomorphic and plesiomorphic) by outgroup comparison (polarity assessment) to an outgroup of non-diseased specimens.

It is also an object of the invention to interpret mass spectrometry data to group specimens into biologically meaningful groups using universal data-mining parsing algorithm to diagnose diseases such as cancer, as well as to differentiate between related diseases, such as between several cancer types.

It is yet another object of the invention to use the predictive power of phyloproteomics and phyloarray as described here to diagnose cancer (class discovery and prediction), and differentiate between several cancer types.

It is another object of the invention to use the predictive power of phyloproteomics and phyloarray as described here using universal data-mining parsing algorithms to forecast deviations in genetic, physiological, and developmental processes, such as susceptibility to cancer (e.g., transitional zone of transitional cases).

It is also an object of the invention to analyze serum proteome or gene expression through the application of a polarity assessment to determine abnormal gene values or protein peaks or expression to graph specimens using phylogenic graphic techniques.

It is another object of the invention to use cellular and molecular validation of the results produced by phyloproteomics and phyloarray as described herein to determine cancer (or other genetic abnormality or disease) developmental pathway, staging, and prognosis, as well post-treatment evaluation based on hierarchical classification of cancer (or other genetic abnormality or disease) specimens into clades.

It is another object of the invention to determine the asynchronicity of gene expressions and their corresponding translated proteins in physiological and pathophysiological conditions.

It is a further object of the invention to decipher the molecular pathways involved in physiological and pathophysiological conditions that could either be used to better understand molecular processes or as therapeutic targets to provide individualized treatments.

Still another object of the invention is to establish the chronological molecular evolutionary continuum from healthy to diseased state.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2A-C are a diagrammatic views of cladograms of showing three types of cancer, created using mass spectrometry data and inventive algorithms according to a preferred embodiment of the invention.

FIG. 3 is a diagrammatic view of a cladogram of showing the dichotomous nature of cancer development, created from inclusive data of three cancers using mass spectrometry data and inventive algorithms according to a preferred embodiment of the invention.

Similar reference characters denote corresponding features consistently throughout the attached drawings.

DETAILED DESCRIPTION OF THE PREFERRED EMBODIMENT(s)

1. Serum Proteome and Mass Spectrometry

Figure 1:
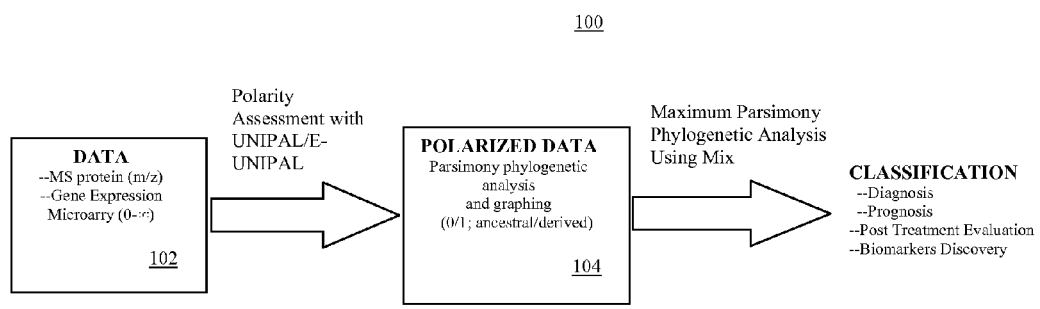
FIG. 1 is a diagrammatic view of the invention according to a preferred method.

While the invention can be applied to among other things, any genetic, physiological, and developmental process, the invention is best described in relation to the application of the invention to the analysis of cancer, due to cancer's evolutionary and multiphastic progression and discrete classifications and types an the ready availability of cancer specimens for validation of the methods disclosed herein. However, the invention is not limited to the study of cancer.

Prior to any description of the application of phylogenetics to cancer serum proteome research, however, it is important to emphasize that despite the broad successful application of systematic phylogenetics to zoology and plant biology for the past fifty years, it has not reached the biomedical research field yet. Classical and molecular phylogenetics has been and still is effectively used in classifying species of viruses, microorganisms, plants or animals based on their evolutionary similarities or derived differences into groups sharing these characters. It is known that cancer development is based on an evolutionary process triggered by progressive mutation accumulations; therefore, biomedicine will gain unexpected benefit from the present application of classical and molecular phylogenetics to cancer and cancer-related research disciplines.

The utilization of the serum proteome to accurately diagnose cancer has been ineffective and its future continues to be surrounded by uncertainties. Although statistical analysis of mass spectrometry (MS) profiles of serum proteins has gained enormous popularity and credibility, algorithmic analysis that produces biologically meaningful results with possible clinical diagnosis is still lacking. It now seems very simplistic to attempt to define cancer on the basis of statistical patterns, since cancer is a multifaceted evolving and adapting cellular condition with multiple proteomic profiles; some of these profiles cannot always be separated from non-cancerous ones by narrowly defined statistical proteomic patterns on the basis of a limited number of spectral peaks. Cancer's incipience is marked by mutations that cause the malfunction of the apoptotic apparatus of the cell, and its promotion is characterized by different phases with each having its distinct proteomic profile. Advanced progression of cancer is marked by cellular dedifferentiation, loss of apoptosis, and metamorphosis into a primordial status where survival, and not function, is the cell's primary mission. In this latter stage, many proteins responsible for differentiation are not produced, and therefore, missing MS peaks are as significant as existing ones in defining the proteomic profiles of cancer.

The multiphase nature of cancer progression combined with possible multiple developmental pathways entail the presence of a large number of proteomic changes for each type of cancer. These factors suggest that the proteomic profile of a cancer type is a hierarchical accumulation of proteomic change over time rather than one or a few simple distinct proteomic patterns. For an analytical tool to be successful in producing a clinical diagnosis, it has to uncover the hierarchical profile of the cancer and be able to place a specimen within this profile.

Phylogenetics has the intrinsic ability to reveal meaningful biological patterns by grouping together truly related specimens better than any other known methods (see Table 1A for a comparison between phylogenetics and clustering). However, phylogenetics alone cannot solve the problem. Proteomic variability encompasses ancestral and derived variations, and only derived m/z intensity values are useful in classifying cancer types and subtypes into a meaningful hierarchy that reflects the phylogeny of their proteomic profiles. For example, all prostate cancer specimens grouped together as truly related specimens (based on their shared derived proteins). While clustering techniques use the presence of common peaks (without resolving their polarity, meaning ancestral or derived) in order to create distinct patterns and then match a specimen to a pattern, parsimony phylogenetics requires polarity assessment, in our case to sort out m/z intensities into derived and ancestral at first, and then uses the distribution pattern of derived values among the specimens to produce their classification into a cladogram as opposed to a dendrogram for clustering. A parsimony cladogram is a distribution map of the derived characters present in a group of specimens while a clustering dendrogram is a branching diagram representing a hierarchy of categories based on average similarity between the specimens or their groups. Using only common intensity peaks without polarity assessment for pattern modeling has proven to be an unreliable means of classification. This is due to the fact that clustering usually involves ancestral values and does not resolve multiple origins of a character (parallelisms), and both result in polyphyletic grouping (having unrelated specimens within a group). Furthermore, since the clustering model is based on a small sample size, it doesn't encompass all of the naturally occurring variations within a cancer type, and therefore, may not produce perfect resolution when encountering a novel specimen. Phylogenetics, on the other hand, can resolve the position of a novel specimen with new variations by placing it in a group that comprises its closest relatives based on the number of apomorphic (derived) mutations it shares with them (Table 1A). Thus, phylogenetics offers not only hierarchy of derived characters but also a seamless dynamic classification.

Cancer can be promptly diagnosed using the present invention, even at early stages, by parsimony phylogenetic analysis of the serum proteome. Since cancer is an evolutionary condition that involves genetic modifications and clonal production, it therefore requires an evolutionary method of analysis. Such an analysis is possible if an algorithm for sorting out the polarity (derived vs. ancestral) of the MS values is available. Through a polarity assessment algorithm (e.g., UNIPAL) that this task can be performed, and MS data can be analyzed with an evolutionary algorithm. The polarity assessment algorithm according to a preferred embodiment of the invention comprises assigning an array representing each protein of the proteome and assigning a weighting, typically "1" to all derived values (i.e., those outside the range of the outgroup normal specimens) and a 0 to all ancestral values (those values within the normal range of the outgroup normal specimens). The number 1 could be replaced by a number weighting the particular derived value relative to other derive values.

For the purposes of this application and its claims, unless explicitly noted otherwise, "range" shall have its ordinary meaning of "all potential values from a lower defined limit to an upper defined limit inclusive."

"Ancestral value ranges" are defined as all of the potential values (e.g., gene expression values or mass spectrometry values) between the minimum and maximum values inclusive found within a tested group of healthy specimens (or "outgroup"). A "derived value" is defined as any value that is not within the respective ancestral value range. For example, within the group of gene expression values found for a particular gene in an outgroup (e.g., "healthy specimens"), the ancestral value range is all values between (and including) the minimum value found and the maximum value found in the outgroup. A derived value for this particular gene would be any value less than the minimum value found or more than the maximum value found. An "ancestral value" is defined as any value within the "ancestral value range." A value must thus either be an ancestral value or a derived value.

"Polarity assessment" is defined as comparing like values (e.g., gene expression values or mass spectrometry values) from a first specimen against the respective ancestral value range for that particular expression or value from an outgroup (e.g., healthy specimens) to determine whether the respective compared values from the first specimen are ancestral values (e.g., "normal") or derived values (e.g, "abnormal").

One aspect of the current invention, Phyloproteomics/Phyloarray, is an evolutionary analytical tool that sorts out mass-to-charge (m/z) or gene-expression values into derived (apomorphic) or ancestral (plesiomorphic) and then classifies specimens according to the distribution pattern of apomorphies into clades (a group comprised of all the specimens sharing the same apomorphies). Phyloproteomics/phyloarray also illustrates the multiphasic nature of cancer by assigning cancer specimens to a hierarchical classification with each hierarchy defined by the apomorphic protein changes that are present in its specimens. The classification is presented in a graphical display called a cladogram. The assumption that all cancerous specimens fit into well-defined proteomic or gene-expression models (patterns based on a few proteomic peaks or expression mean) that distinguish them from non-cancerous ones is replaced here by phylogenetically-distinct clades of specimens with each clade sharing unique derived protein or expression changes (synapomorphies) among its specimens.

TABLE 1A

The advantages of phylogenetic analysis over statistical cluster analysis.

| Phylogenetic Analysis | Cluster Analysis |
| --- | --- |
| Produces a classification based on shared derived similarities and reflects phyletic/developmental relationships | Produces a classification based on overall similarity and does not reflect phyletic relationship |
| Uses a universal algorithm for all types of cancers | May require a specific algorithm for each cancer type |
| Discriminates between ancestral and derived states; uses only derived character states (apomorphies) | Does not discriminate between ancestral and derived character states; uses both |
| Resolves issues of parallelism (multiple independent origins) by parsimony | Does not resolve issues of parallelism |
| Offers predictivity. | Does not offer any predictivity. |

A. Data Collection and Computation

A.1. Description of the Computational Application

As a computational platform, phyloproteomics/phyloarray encompass two universal algorithms that are run consecutively to produce the classification of specimens:

First, UNIPAL (or its later version E-UNIPAL): Universal Parsing Algorithm. This is a newly developed program to perform outgroup comparison (polarity assessment) on the specimens' MS or expression values. In order to assess the usefulness of each MS or expression value, a polarity assessment has to indicate whether the m/z or expression value is a derived or ancestral state. Then it is given a score to indicate its state. An array of each MS point (or a subset thereof such as an array containing only an MS point if at least one specimen has a derived state) is created with a score (preferably 1 or 0) for each MS point. A weighted score may be provided (i.e., other than 1) for each derived state if more or less weight should be factored for a particular MS state (e.g., to reduce scatter).

In further detail, the UNIPAL program reads an entire MS serum data set of healthy specimen (or the "outgroup") and extracts the absolute minimum and maximum for every row in the matrix (i.e., for each corresponding position of the specimens). The result is separated into two vectors: one vector has the absolute minimum and the other has the absolute maximum of the values of the original matrix.

The program then reads another data set of interest (cancerous for example) and compares each value for each specimen to the value of its corresponding position against the minimum ("min") and maximum ("max") vectors. If a value at hand is within the minimum-maximum range, it is mapped to 0 (indicating an ancestral/normal state) in an associated vector. Otherwise, it is mapped to 1 (indicating a derived/abnormal state) in the vector, resulting in an array of 1s and 0s. Of course, as discussed below, a weighting for each position could be assigned instead of solely 1s and 0s.

Analogously, for micro array, the program can also extract the apomorphic, up-regulated, down-regulated and mixed genes and their positions in the matrix to create an array of 1s and 0s (or proper weighting).

Second, a parsimony phylogenetic program, preferably MIX (part of the package of PHYLIP: Phylogeny Inference Package, ver. 3.57). This is one of the best-known prior art, phylogenetic packages. It includes several programs to carry out phylogenetic analysis on various data sets. For the phylogenetic analysis of data set, MIX is used for parsimony analysis. One skilled in the art would recognize that other parsimony analysis algorithms could also be used. A parsimony analysis is one that produces a classification with the minimum amount of steps; it attempts to lessen multiple origins of a change (0 to 1) or reversals (1 to 0). A parsimonious hypothesis is the one with the least amount of ad hoc hypotheses.

In relation to MS proteomic data (m/z values), UNIPAL/E-UIPAL evaluates each point of the spectrum to find out one of four conditions in the specimen under study:

1. Is it a new novel peak that doesn't occur in any of the normal specimens (the outgroup)?
2. Is it a vanished peak that otherwise exists in all of the normal specimens?
3. Is it an upregulated protein, i.e., exists at higher concentrations than in the normal specimens?
4. Is it a downregulated protein, i.e., exists at lower concentrations than in the normal specimens?

In relation to microarray gene-expression values, UNIPAL/E-UNIPAL evaluates each expression value of a specimen to find out one of three conditions:

1. Is it an overexpressed in relation to the range of the normal specimens?
2. Is it underexpressed in relation to the range of the normal specimens?
3. Is it dichotomously expressed in relation to the range of the normal specimens?

All of these four conditions of MS and three of gene-expression are treated as equal events and are preferably given an equal weight when scored. Once UNIPAL carries out polarity assessment for all the specimens under study (i.e., the study collection), the scores are produced in an input file that complied with PHYLIP-MIX's input requirements. UNIPAL a novel, polarity assessment program that is designed to work with MS and gene-expression data and produce a listing of novel derived values in a coded format.

The second algorithm is a popular, prior art phylogenetic parsimony program, PHYLIP-MIX, that uses the values generated by the first algorithm (UNIPAL) to classify the specimens. PHYLIP is a robust analytical package that has been tested by scientists for the past 16 years, and is probably the most cited in phylogenetic studies. An added benefit to this universal approach is that it makes possible the comparison between results from different data sets, and the evaluation of competing analytical tools. PHYLIP-MIX processes the input file according to Wagner's parsimony and produces the most parsimonious (or several equally parsimonious) organization of relationships in a graphical format termed cladogram(s). See for example, FIG. 3.

FIG. 1 is a schematic representation of phyloproteomic analysis. The process involves two main steps. The first is the algorithmic sorting of the m/z values into derived (exists in some but not all specimens) and ancestral (exists in all specimens); the derived values are those signifying either a novel, vanished, or up and down regulated peak. The second step is a parsimony phylogenetic analysis that groups the specimens on the basis of the shared derived values. The implementation of these steps is discussed below using data generated for an exemplary set of serum proteins:

A.2. Data Collection

Example 1

A mass spectrometry (MS) data of serum proteins was generated by surface-enhanced laser desorption-ionization time-of-flight (SELDI-TOF) of 460 specimens from three types of cancer: ovarian (n=143), pancreatic (n=70), and prostate (n=36), as well as from non-cancerous specimens (n=211). See FIG. 4. All sets of data used in samples were available from the NCI-FDA Clinical Proteomics Program, and are referred to in a few publications (home.ccr.cancer.gov/ncifdaproteomics/ppatterns.asp).

A.3. Results

A phylogenetic tree termed cladogram that shows the hierarchical classification in a graphical format best illustrates the results of a phylogenetic analysis. Parsimony analysis produced one most parsimonious cladogram (requiring the least amount of steps in constructing a classification of specimens) for each of the pancreatic and prostate specimens (FIGS. 2A & B), 5 equally parsimonious cladograms for ovarian specimens (FIG. 2C shows only one), and several equally parsimonious cladograms for the inclusive analysis (FIG. 3, summarizes only one). Multiple equally parsimonious cladograms were fundamentally similar in topography and differed only in the internal arrangement of some minor branches.

A complete separation of the cancer specimens from non-cancerous ones depended on the size of the non-cancerous outgroup (healthy) used to carry out polarity assessment. Polarizing the m/z values with the largest size outgroups (ones encompassing the largest amount of variation) available for each cancer type produced cladograms with differential groupings of cancerous and non-cancerous specimens separately, i.e., no cancer specimens grouped with the healthy and vice versa (100% sensitivity and specificity). However, with the use of randomly selected smaller outgroups, sensitivity dropped to 96%; this illustrates the significance of using the largest number possible for outgroup polarity assessment.

Each of the cladograms for the data of Example 1 (FIG. 2A-C) shows an upper bifurcation composed of cancerous specimens, while the lower end of the cladogram was occupied by a number of basal clades composed of non-cancerous specimens; and a central assemblage of non-cancerous clades adjacent to cancerous ones. The latter assembly formed a distinct order of well-resolved and mostly single-specimen clades in the middle of the cladogram nested between the cancer and healthy clades (bracketed arrows in FIGS. 2A-C); we termed them transitional clades (TC). The transitional clades bordered their respective types (cancer or non-cancer) in a tandem arrangement that formed a transitional zone (TZ) between the non-cancer and cancer clades.

When data of all specimens of the three cancer types (ovarian, pancreatic, prostate) were pooled together with non-cancerous ones and processed, each of the three cancers formed two large clades (the terminal and middle) and numerous small transitional clades adjacent to the non-cancerous ones (FIG. 3). The pancreatic and prostate clades formed sister groups in their terminal and middle clades, and their terminal clades were nested within the ovarian clades. The ovarian specimens formed two distinct clades at the upper part of the cladogram.

The cladograms revealed greater similarities in topography among cancer types. For each of the three cancer types, there were two large recognizable clades (the terminal and the middle) forming a major dichotomy that encompassed the majority of the specimens of each type (FIG. 2A-C). This dichotomy persisted in the inclusive cladogram as well (FIG. 3), with each of the cancers having two major clades.

FIG. 3 shows a phyloproteomic analysis showing dichotomous distribution of cancers into two clades and a clean separation of the healthy outgroup. A schematic cladogram obtained after a comprehensive phyloproteomic analysis inclusive of 460 specimens representing ovarian, pancreatic, and prostate cancers as well as non-cancerous specimens ([390×15,000]+[70×8,000] m/z values). Only a schematic depiction of the inclusive cladogram is presented here in order to better illustrate the parsimonious distribution of the clades as the substantial number of all specimens together generated a very busy cladogram. Indeed, each bifurcating lane is representing scores of specimens, e.g. there are over 200 healthy specimens within the healthy clade. Specimens of every cancer type are classified into two clades: a terminal and middle, as well as transitional clades. Healthy specimens are classified into a major healthy clade and transitional clades.

A.4. Advantages over the Prior Art

Prior to the present invention, no one has attempted to apply a universal phylogenetic algorithm to MS serum proteomic data for genetic, physiological, and developmental processes analysis where deviation from the normal conditions of the population need to be assessed or profiled, such as the analysis of cancer. By developing and applying an algorithm for polarity assessment and then using a parsimony phylogenetic algorithm for classifying specimens of three cancer types (ovarian, pancreatic, and prostate) it has been demonstrated that phylogenetics can successfully be applied to MS serum proteomic data for analysis, diagnosis, typing, and susceptibility assessment. Additionally, phyloproteomics points out the presence of distinct trends within cancer that render protein profiling by statistical and clustering phenetic methods inaccurate, unpredictive, and at least practically ineffective for diagnostic purposes of transitional cases (i.e., specimens with a minimum number of mutations that cannot yet be diagnosed as cancerous by microscopy or immunohistochemistry).

Thus far, the number of algorithms used for MS serum analysis is almost as equal to the number of published reports, and none has been tested on more than one type of cancer. Reproducibility and comparability of proteomic analyses are unachievable due to the lack of broadly acceptable universal methods of analysis. The present invention introduces a universal approach to the analysis of MS serum data. Phyloproteomics is composed of two algorithms that are universally applicable to MS data of any cancer (FIG. 1).

Phylogenetics is different than phenetic statistical clustering. Phylogenetics has the intrinsic ability to reveal meaningful biological patterns of physiological and pathophysiological conditions by grouping together truly related specimens better than any other known methods (Table 1A). Proteomic variability encompasses ancestral and derived variations, but only derived m/z intensity values are useful in classifying cancer types and subtypes into a meaningful hierarchy that reflects the phylogeny of their proteomic profiles. While clustering techniques use the presence of common peaks (without resolving their polarity) in order to create distinct patterns and then match a specimen into a pattern, phylogenetics requires polarity assessment to sort out m/z intensities into derived and ancestral at first, and then uses the parsimonious distribution pattern of derived values among the specimens to produce their classification (i.e., the cladogram). Using only common intensity peaks without polarity assessment for pattern modeling has proven to be an unreliable means of classification. This is due to the fact that clustering usually involves ancestral values and does not resolve multiple origins of a character (parallelisms), and both result in polyphyletic grouping (having unrelated specimens). Furthermore, since the clustering model is based on a small sample size, it doesn't encompass all of the naturally occurring variations within a cancer type, and therefore, may not produce perfect resolution when encountering a novel specimen. Phylogenetics, on the other hand, can resolve the position of a novel specimen with new variations by placing it in a group that comprises its closest relatives based on the number of apomorphic mutations it shares with them (Table 1A)

Phyloproteomics has a potential for predictivity in for example cancer. Predictivity here is defined as the capacity of the classification to predict the characteristics of a specimen by knowing the specimen's location within a cladogram. By using an ample number of well-characterized cancer specimens in an analysis, the unknown characters of a new specimen will be forecasted when it assembles within a clade in the cladogram. The specimen's location in a cladogram is always based on the type of mutations it carries and shares with the clade members, which will determine the diagnosis, cancer type, or the susceptibility to developing cancer. Cladogram topography shows a hierarchical accumulation of novel serum protein changes across a continuum spanning from the transitional non-cancerous specimens to the cancerous ones, with the latter having the highest number of apomorphic mutations.

Phyloproteomics can reveal dichotomies in cancer development. Cladograms also reveal that the three types of cancers have fundamentally similar topographies; they all have one major dichotomy that indicates two lineages within each type (represented on the cladograms by the terminal clade and the middle clade [FIGS. 2-3]). If this typification should hold true for additional cancer types, then it is possible that ontogenetically all types of cancers undergo two major common pathways in their development. There are only a few recent reports that support a dichotomous pattern of development in colorectal cancer, glioblastomas, and pancreatic carcinoma. Dichotomies may arise in cancer development due to the selective advantages of cells harboring mutations; the surviving mutations can be genetic or chromosomal, point mutation or amplification, or differential expression of alleles.

Non-cancerous transitional clades, present in all cladograms and mostly comprised of individual specimens, are the closest sister groups to cancer clades. Because of their proximity to cancer clades, these specimens, assumed to be from cancer-free individuals, represent the early stages of cancer development that cannot yet be morphologically or microscopically diagnosed as cancerous.

Phyloproteomics also reveals the individuals "at risk" to developing cancer. For diagnostic purposes, cancerous and non-cancerous transitional specimens will always be challenging to classify by clustering and other statistical techniques. Occasionally, these specimens are distinct from one another by only very few apomorphies. The mostly single specimen composition of the transitional clades attests to their uniqueness, and therefore, trained statistical algorithms that search for certain peaks will most likely fail to assign them to the correct category. However, in phyloproteomics, the number of synapomorphies they share with other specimens determines their location on the cladogram. Current diagnosis of cancer is not based on the number of mutations or synapomorphies; therefore, the determination of the status of a transitional specimen is subjective without a clear definition that is based on derived mutations established by pathologists. Applicant have found that the position of a transitional specimen within the transitional zone determines its diagnosis; if a specimen is on the upper end of the transitional zone (i.e., bordering cancer clades), then it is a cancerous specimen (cancer still microscopically undetectable), and those occurring in the middle and lower end of the transitional zone to be called high risk specimens. Tests to date have proven that this is theoretically sound (see for example, confirmation in the microarray gene-expression analyses).

B. Research Design and Methods

B.1. Research Design

The crux of our research has been based on the resolving capability of SELDI-TOF-MS technology to detect the variations between diseased and healthy specimens. Our parsing algorithm, UNIPAL, utilizes this discriminatory power to produce a polarity assessment of MS values into derived and ancestral, and then PHYLIP-MIX uses the polarized values to construct the relationships between these specimens—the classification. Applicants have found that:

UNIPAL can be used as a preferred qualitative and quantitative universal data-mining parsing algorithm ("UNIPAL") for sorting out MS cancer serum proteomic variations into derived and ancestral states (apomorphic and plesiomorphic).

UNIPAL detects qualitative variations of cancer serum proteome. Cancerous cells possess altered protein metabolism, and their proteomic profiles have either new proteins, or some of their normal proteins are no longer produced. By parsing through MS data, algorithmic computer programs try to uncover the differences between cancerous and non-cancerous specimens. From a qualitative point of view, we designed UNIPAL to maximally recognize new or vanished protein peaks within each specimen. The algorithm will compare the MS data of the specimen under study to that of a set of normal specimens, and scores newly risen or vanished peaks as derived states. These two events are given equal weight.

Alternatively, the normal specimens can be combined to form a "super outgroup" containing a range of values for each protein in the serum proteome to which later samples can be compared. The super outgroup is a hypothetical outgroup that encompasses a data summary of two or more outgroup specimens and is used in their place as an outgroup to run an analysis/diagnosis. This "super outgroup" may be altered over time as more specimens are analyzed and the range of normal specimens is fine tuned or for different purposes or applications.

A study was carried out by using sets of non-cancerous human specimens as outgroups for the analysis of ovarian, pancreatic, and prostate cancers. However, in a preferred method of differentiating derived states from ancestral states, the specimens defining the outgroup is preferably composed of a non-human species such as chimpanzee (*Pan troglodytes*). The chimpanzee is considered the closest biological relative. Using the closest relative as the outgroup is a standard phylogenetic technique that uncovers the deviations within the study group—humans. The advantage of non-human outgroup is that it permits a more accurate polarity assessment of human MS values where only unique cancer values would be identified and used later by the phylogenetic program to delimit cancerous clades. Therefore, the qualitative parsing power of UNIPAL preferably includes using chimpanzee MS serum data as the outgroup. No less than 50 chimpanzee serum specimens are preferably used. These may be available through either collaborators or commercial sources to acquire their MS profile to use as the outgroup in a phyloproteomic analysis. Additionally, a more detailed cladogram may be available by increasing the number of specimens used. Preferably, 500 specimens of non-cancerous human serum, and 500 cancerous specimens representing no less than 7 cancer types (breast, colon, lung, liver, ovarian, prostate, and pancreatic) to test the qualitative detection power of phyloproteomics will be used.

UNIPAL detects quantitative variations of cancer serum proteome. Quantitative protein variations in cancerous specimens may be manifested in either up- or down-regulations. Absolute quantitation by SELDI-TOF-MS is impossible, but relative quantitation is attainable. Therefore, UNIPAL detects an increase or a decrease of a peak's value in relation to the range of normal specimens as derived states. An increase or a decrease is scored with equal weight.

As described above, an optimum outgroup comparison should be established with at least 50 chimpanzee sera, and the polarity assessment of quantitative MS values will be established for the human specimens.

In our study, we have scored the derived qualitative and quantitative as equals. However, in a further preferred method of analysis, higher weight may be given to states to qualitative over quantitative values, given their dramatic effect on the cells affected, which may lead to more accurate results. UNIPAL can be modified to give a higher score for a qualitative value than quantitative one, and the effect on the analysis results can be evaluated to determine which method provides the most accurate results for the specimen. It would then be easy to pinpoint the effect of qualitative versus quantitative on the classification.

The invention can be used for the predictive power of phyloproteomics to diagnose cancer, and differentiate between several cancer types.

Phyloproteomics categorizes a cancer specimen into its type and subtypes on the basis of their phylogeny (origin and ontogeny [developmental pathways]). An intrinsic characteristic of a phylogenetic classification is its predictivity; each of its groups' characteristics are shared by all of its members and any newly added members, i.e., the specimen's characteristics, are revealed when its place in the classification becomes known—location on the cladogram. In a phylogenetic sense, when the program places a specimen in a group, it is grouped with its closest relatives—the most genetically similar specimens to each other. This type of classification reflects the phylogeny of the group, and also the groups' relationship to other groups as illustrated by the cladogram. Therefore, when a specimen is classified with cancerous specimens then it is cancerous, and since different types of cancers occupy different branches of the cladogram, phyloproteomics may produce the diagnosis and the type.

The predictive power of phyloproteomics may be further confirmed with specimens of known clinical history. Analysis has shown that diagnosis is achievable with phyloproteomics since the specimens' diagnosis was known (type of cancer or healthy). However, the invention can be used to validate the predictivity by analysis against a different set of outgroup specimens. As described above, in a preferred embodiment of the invention, at least 50 specimens of chimpanzee serum are used as outgroup, 500 specimens of non-cancerous human serum, and 500 cancerous specimens representing no less than 7 cancer types (breast, colon, lung, liver, ovarian, prostate, and pancreatic) to further confirm the predictive power of phyloproteomics to diagnose cancer and type it, and also to study the ontogenetic relationships among the cancer types.

The invention can be used to forecast susceptibility to developing cancer.

Phyloproteomics predicts the susceptibility to developing cancer based on the location of the specimen on a cladogram. The multiphasic nature of cancer dictates that cancerous specimens do not carry equal number of mutations, and some types of cancers have two or more developmental pathways with each pathway having its own set of mutations. Furthermore, some non-cancerous specimens carry the initial mutations of a cancer that has not yet shown its morphological manifestations; we termed these transitional specimens. Our results confirm the presence of transitional specimens that occupy a nested position between the cancerous and non-cancerous branches of the cladogram. These specimens appear to lack the full assortment of derived features that would otherwise have placed them in the cancer groupings (clades), however, the specimens of interest here are those that have not been diagnosed as cancerous but seem to have accumulated a good number of derived states that placed them as the closest sister group to some cancerous groups.

The invention can be used to determine cancer developmental pathway(s), staging, and prognosis.

The hierarchical arrangement of a cladogram reflects the developmental pathway and stage of cancer progression of the specimens. The hierarchical arrangement of the cancerous specimens into a cladogram reflects a cumulative gradient of derived states, i.e., the terminal clades of a cladogram possess a larger number of mutations. A larger number of mutations may reflect advanced stages of the disease with poor prognosis. By comparing the locations of specimens on the cladogram and their respective patients' health condition, the cladogram is used in a preferred method of determining cancer staging in patients. This method will be used to determine a patient's cancer stage based on the number of mutations (i.e., derived states) that are detected in serum mass spectra. The phylogenetic program, PHYLIP-MIX, lists all the derived peaks that are involved in delineating a clade. Therefore, the derived protein/peptides that define a clade can easily be retrieved and biochemically characterized.

This method offers a new objective method for staging cancerous patients and determination of the treatment regimen. By extrapolating on the same reasoning, the patient prognosis and post-treatment evaluation may also be predicted on the basis of their specimen location on the cladogram.

The invention can utilize cellular and molecular validation of the results produced by phyloproteomics.

Diagnosis obtained by phyloproteomics correlates to clinical diagnosis of testing set(s) and blinded set(s). Tests may be consecutively carried out to assess the validity of results obtained from phyloproteomic analysis in other areas. The first is preferably a testing set where the specimens' diagnoses are known. These test specimens will be used to further fine tune the accuracy of phyloproteomics to accurately place them in their respective clades, i.e., correct diagnosis. The second set is preferably a blinded validation test set of specimens. Mass spectra of blinded specimens encompassing cancerous and healthy will be used to validate the ability of phyloproteomics to produce accurate diagnosis. Phyloproteomics should pass the two tests with sensitivity and specificity above 99%.

Susceptibility cases (at risk group) should be congruent with molecular and biochemical tests to confirm the presence of mutations.

Predisposition to cancer is seeded in stem cells carrying mutations, which are responsible for late-life somatic cancers. One of the main contributions of phyloproteomics is its delineation of a susceptible group to cancer development. As the inclusive cladogram (FIG. 3) shows, this group is located below cancerous clades but above the non-cancerous ones on the cladogram. Since this group of individuals is asymptomatic, then genetic and/or molecular investigation for mutations is the only confirmation for the validity of susceptibility. Initial testing may be performed for known general mutations that confer a predisposition for cancer. The following mutations can be tested for: BRCA1 & 2 for breast and ovarian cancers; CHC1-L for prostate cancer; hMLH1, hMSH2, hMSH6, and hPMS2 for colorectal cancer; fumarate hydratase gene and XRCC1, XPC, ERCC1, XRCC3, and XRCC7 for renal cell carcinoma (RCC); MTHFR for lymphoid malignancies; p53 for chronic lymphocytic leukaemia (CLL); and Ras for general predisposition.

Phyloproteomics is a clinical diagnostic tool.

Phyloproteomics is a useful clinical tool to predict and diagnose cancer in a clinical setting. The phyloproteomic paradigm presented herein validates the premise that SELDI-TOF-MS of serum proteins contains diagnostic indicators to accurately separate cancerous from non-cancerous specimens, typify cancers, and list susceptible specimens. Phyloproteomics' readiness as a diagnostic tool is validatable. The analytical procedure of the present invention can be used as integral stand-alone computer program to be used in a clinical setting.

Preferably the invention in a preferred embodiment of the invention can be distributed with specific instructions for running serum specimens on mass spectrometry machines, including a user-friendly interface for entering data, and an output program with interpretation of results.

B.2. Preferred Methodology and Apparatus for Performing the Same

UNIPAL—Bioinformatics algorithm for polarity assessment. UNIPAL developed by the team is universal as stated above. The assessment method can be applied to other high throughput technologies such as genomics, and gene and protein microarray data. These techniques can also be analyzed on their molecular changes (derived) in comparison to a control (ancestral) and their assemblage into clades sharing same synapomorphies. UNIPAL/E-UNIPAL has been used in analyzing a few sets of gene microarray data from different tissues and cell lines such as gastric cancer, leiomyosarcoma, melanoma, and prostate tissue specimens (described further below). The results showed a clear separation within various sets of benign fibroids and leiomyosarcoma; primary and metastatic prostate cancer; as well as the various cell lines and tissues of melanoma.

Phyloproteomics: a dynamic method of classification. Other profiling techniques aim at fitting the specimen's profile into a few patterns generated by statistical programs, where each pattern represents a given state of the disease, and compare each specimen to these patterns throughout the continuum of disease development. It is known that the proteomic make up is not a static event and the patient's profile might change throughout the disease progression. Phyloproteomics, however, is not only universal but also a dynamic process of sorting out the proteomic changes at any given time throughout disease development by placing the patient according to his or her disease state in the respective category of the clade classification: healthy but in the transitional clade, cancer but in transitional clade (presence of molecular changes detectable in the serum but cancer still undetectable by the imaging technology available), or in the cancer category clade. For example, when we consider the theoretical case of a patient who comes to the clinic at year one with prostate hypertrophy, he will categorize within the transitional clade between the healthy and cancer bifurcation. At year 5, the same patient, although showing similar PSA levels will nest in the cancer clade, meaning that his serum protein make up has changed but no signs of cancer are yet detectable. Based on our methodological approach, this patient should be followed even more closely despite the negative routine clinical tests. At year 7, the same patient will be diagnosed with stage three prostate cancer and of course his serum protein analysis will place him at the top end of the clade, which is representative of the more advanced cancer stages. This example illustrates the dynamic processing of our method throughout the continuum of disease development and progression or transition from healthy to disease states.

Mass Spectrometry

Mass spectrometry includes a broad range of various analytic methods that share certain common features. In simple words, they all use a sample presentation structure, an ion source, a mass analyzer, and an ion detector. The role of a mass spectrometer in the life sciences is to separate charged molecules based on their molecular mass and to measure their mass numbers thus determining their mass-to-charge ratios (m/z).

Matrix-Assisted Laser Desorption/Ionization Mass Spectrometry (MALDI-MS)

In a preferred embodiment of the invention, MALDI-MS is used for its large collection of high throughput technologies utilized for proteomics studies. It is widely used due to its wide mass range of detection. During the MALDI process, ions are generated from the analyte and interact with the matrix that absorbs at the wavelength of laser irradiation. The laser excitation causes desorption and ionization of the specimen. The irradiated peptide ions accelerate and approach a detector at different time intervals thus the name of time of flight (MALDI-TOF). The resulting mass spectra are mass to charge (m/z) ratio values in which the intensity of peaks is correlated to the peptides concentration in the analyzed fraction. Due to the complexity of the protein/peptide mixtures and the presence of potential contaminants that can affect the measurement outcomes, variations of the experimental parameters are recognized as alternatives, such as the dried-droplet method, the use of a fast-evaporating solvent, addition of nitrocellulose, or water soluble acids. Instead of using the mixture with different matrix conditions to acquire the largest amount of peaks identifying as many components as possible from the same sample, liquid chromatography (LC) to fractionate the protein mixture has usually been used prior to the MALDI-MS (LC-MS). If the aim is peptide mass mapping and protein identification, a water insoluble matrix, such as α-cyano-4-hydroxy cinnamic acid, would be the method of choice. For a more heterogeneous sample profile, the dried droplet approach is better using water-soluble matrix compounds. Of course the choice of the appropriate experimental method to analyze serum proteins will depend on the subset of the proteome to be studied. The advantage of our data mining platform is that it is inclusive and non-discriminatory which means that the results obtained from different mass spectrometer matrices could be all polarized into ancestral and derived, and classified hierarchically into a cladogram (regardless of the changeability of the experimental protocol).

Surface Enhanced Laser Desorption/Ionization (SELDI)

SELDI-TOF is considered an improved approach to MALDI-TOF-MS that is not only able to uncover single protein biomarkers but is also able to categorize biomarker expression patterns and may be used in an alternative embodiment of the invention. There are numerous other advantages to the SELDI-TOF-MS use, such as its tolerance for salts and impurities, low amount of material (1-10 µg), wide range of sample volume (0.5-400 µl), and a reasonable array of protein/peptide molecular weights (1,500-20,000 Da). Of the major advances in the SELDI-TOF-MS technology is the use of the ProteinChip® system (Ciphergen Biosystems Inc.) that provides chromatographic surfaces with a number of physicochemical characteristics: hydrophilic, hydrophobic, cationic, anionic, metal ion surface, or even coated to capture or bind specific class of molecules. The data used in at least one example of the present invention for our bioinformatics analysis were retrieved from home.ccr.cancer.gov/ncifdaproteomies/ppatterns.asp. In brief, the Applicants used a C16 hydrophobic interaction protein chip analyzed on the Protein Biology System 2 SELDI-TOF-MS (Ciphergen Biosystems, Freemont, Calif.). The sera mixtures containing peptides and proteins below 20,000 m/z array were ionized with α-cyano-4-hydroxy-cinnamic acid using the following analytical conditions: laser intensity 240, detector sensitivity 10, mass focus 6000, position 50, molecular mass range 0-20,000 Da, and 50 shots/sample. The controls were subjected to the same procedure alongside the samples in a random distribution on the same chip and on multiple chips. Recently, this method has been challenged for having generated low resolution spectra and for being designed as a research-grade platform and not as a routine clinical tool. Thus, a high resolution approach has been adopted to reduce the machine-type use variability and the time interval drifts. This was obtained by using the hybrid quadrupole time-of-flight (QqTOF-MS). On the flip side, the Qq-TOF-MS high resolution generated sets added to the complexity and dimensionality of the data and reduced the likelihood of meaningful pattern discovery. More sophisticated MS techniques are being developed and applied to proteomics, which may be used without departing from the scope of the invention. Two-dimensional separations coupled with Fourier-transform ion cyclotron resonance, TOF-MS (2DFT-ICR TOF-MS) and strong cation exchange has shown 10-fold improvement in peak capacity over the above mentioned techniques.

It should be emphasized that the UNIPAL sorting power is independent from the above-mentioned technical considerations and analysis limitations as it is designed to include high number of data sets generated by any machine at any given time in a reproducible and accurate fashion with high specificity and sensitivity.

Peptide Sequencing and Protein Identification

In a further preferred embodiment, biomarkers may be identified as an additional step of the preferred embodiment. With UNIPAL it is, in fact, easy to extract the exact protein sets characterizing the clade (meaning the protein biosignature, characterizing a group of patients that is not shared with the normal controls). The National Center for Biotechnology Information's nonredundant protein sequence database (NCBInr), that includes entries from GenPept, SwissProt, PIR (a Georgetown University-based database), PDF, PDB and RefSeq, can be utilized for such.

Multiplex Analysis

Several techniques can be used in protein studies, such as 2-dimensional polyacrylamide gel electrophoresis (2D-PAGE), Western blotting, immunostaining, radioimmunologic (RIA), and single enzyme-linked immunosorbent assays (ELISA), which are now considered low throughput methodologies, time consuming, and requiring high amounts of sample material.

For this high throughput MS proteomics study, it is preferred to use high throughput functional protein mapping. Protein microarrays are increasingly being used especially that there is an extensive support network for instrumentation and applications for multiplexed biomarkers. This technique can be used following definition of the protein bio-signature involved in a particular biological process. There are array panels already developed for endocrine and cardiovascular diseases as well as cytokine/chemokine profiles. Other multiplexed arrays could be tailored to systems-oriented investigations. The layered peptide array (LPA) technique, for example, has recently seriously been considered for clinical studies including cancer, infection, and autoimmune diseases using sera and saliva specimens. By using LPA platform prototype, Gannot and colleagues showed that 5000 measurements could be achieved in one experiment. We are planning on using this technology in year three and four of the proposal.

Serum Sample Collection

Sera for other types of cancer can be either purchased or obtained through collaborations with other medical institutions and organizations. Primate non-human ("non-human primate") specimens can also be purchased. As a further advantage, the specimens may be studied without requiring any identifiable private information regarding the individuals providing the serum specimen.

Statistical Analysis

We will apply classification procedures, such as phylogenetic classification trees and its several variants, to relate the derived states to the disease status. The sheer number of derived states precludes the use of classical parametric approaches to determine patterns of protein associated with the case-control label. Interactions between proteins are likely to be important. Hence, statistical methodologies that are able to uncover potential interactions should be utilized. This consideration points to recursive partitioning as currently the only possible method of analysis. In its non-parametric version (later extensions call on simple models), it is not restricted to linear relationships. It is particularly useful in bringing interactions into light. Parametric approaches, such as logistic regression, rely on some prior knowledge (or some lucky guess) in order to include the relevant interaction parameters, and current teaching requires that lower-order terms be included whenever interactions appear in a model (e.g., no first-order interaction without main effects, no second-order interactions without all first-order interactions). By working with (increasingly homogeneous) subsets of the data, recursive partitioning can bring out complex pathways that would require a large number of parameters in classical paradigms.

In particular, the CART package may be used to perform this type of analysis. Other programs such as QUEST, while able to deal with categorical outcome variables, were not developed for such variables and may require transforming them. Other versions of the CART algorithm may be developed that more fully explore the space of decision trees and that allow the predictive worth of the resulting model to be tested.

A classification tree attempts to predict an outcome (here, disease status) from a set of explanatory variables (here, the peak status). In doing so, it efficiently sifts through large numbers of explanatory variables. The procedure starts with putting all the data at the root of the tree (the best predictor is then the group with the highest frequency). For each covariate, realized values are examined for their ability to discriminate between the two groups. The best covariate is selected (i.e. that covariate with the lowest misclassification cost) and the data set are divided into two more homogeneous subsets (with respect to the treatment label). The procedure is repeated on each subset separately. The tree is grown until all terminal nodes are pure (they contain observations with the same disease label) or they contain too low a number of observations to allow further splitting (this threshold is set by the investigator). The resulting tree yields an underestimate of the actual misclassification cost. To remedy this, the tree is pruned via cross-validation. Several terminal nodes may have the same treatment label. The path from each terminal node via the internal nodes to the root is traced to yield a classification rules, i.e. a combination of covariates thresholds. Hence, several rules may be associated with the disease group.

The results of such the classification analyses will be verified by fitting logistic regression models that include parameters for the highlighted interactions (backward elimination will be utilized to obtain the most parsimonious model). Model selection will be performed predictively using prequential test statistics. The evaluation is based solely on probabilities a model generates for future events. These forecasts will be measured against the outcomes via a scoring rule. We select a starting set of observations (usually, the first few observations) to produce the first parameter estimates. All other data points serve, in turn, two purposes: validation and estimation.

What is described here can be regarded as sequential cross-validation. While (classical) cross-validation involves changing information sets of constant size, here one deals with an information set that increases with each new fit of the model. Each new data point involves a single re-estimation of the parameters. This set-up is more amenable to formal testing than cross-validation.

Serum Proteome Summary

Phyloproteomics offers a new paradigm in physiological and pathophysiological analysis, for example cancer, that reveals relatedness and diversity of specimens in a phylogenetic sense; its predictive power is a useful tool for diagnosis, characterizing cancer types, and identifying universal characteristics that transcend several types of cancer. The implications of the new paradigm are of valuable clinical, academic, and scientific value.

To summarize an aspect of our novel approach and its relevance to biomedical sciences, we include a series of clinical scenarios that better illustrate phyloproteomics application.

Scenario A: Routine Annual Check-Up

A healthy person visits his/her primary physician for the routine check-up and a serum sample is taken for the routine laboratory tests. This time a fraction is submitted to MS and the spectra are analyzed using phyloproteomics. After comparison of the serum to over a 1,000 other healthy and cancer specimens, this person's bio-signature is sorted out in the healthy clade. Thus, the person is "absolutely healthy".

Scenario B: Prevention

Two years later, the same person visits the physician for the same routine check-up. After analyzing the serum with the phyloproteomic approach, this person's bio-signature is sorted out in the transitional clade nested between the healthy and cancer specimens. So, the person is healthy but his/her molecular bio-signature is, this time, distinguishing him/her from the absolute healthy. This means that molecular changing are occurring but have not reached yet the "macroscopic" clinical manifestations. At that point in time, the routine laboratory tests are all negative and the physician's verdict would be that the person is "healthy". In the new medical paradigm offered by the phyloproteomics analysis this person would be "at risk" of developing cancer. Preventive medicine could play a major role in this case. The physician, in this case, could recommend that the patient changes the life style, diet, and environment. Thus, the molecular changes might never translate into a disease during the patient's lifespan.

Scenario C: Diagnosis

If this person ignores the recommendations and two years later comes back for the routine medical visit, the laboratory tests show irregular readings. The MS data will in this case not only classify him/her in the cancer clade but also in the respective type of cancer category coinciding with macroscopic clinical manifestations. Thus, the patient has developed "cancer".

Scenario D: Prognosis

Depending on the position of this patient on the clade (basal, middle, or terminal), one could determine the cancer clinical stage. Thus, the physician could convey a prognosis based on the "stage of cancer".

Note: The time frame for developing cancer given in these different scenarios is arbitrary. In real life, mutations can accumulate throughout the lifetime of an individual but at an unknown speed. It could be as long as an 85 year old man develops cancer late in life or a 6 month infant having a brain tumor.

2. Gene Expression Datasets

Advances in targeted individualized treatment of cancer and other physiological and pathophysiological conditions will only progress when a highly predictive classification model becomes available where class discovery and prediction are based on an evolutionary paradigm. Current gene-listing, gene-linkage, and clustering do not resolve interplatform comparability and reliability, and are incongruent with the nature of cancer progression. An accurate and predictive analytical model should account for development patterns of examined conditions, such as the multiphastic nature of cancer, and be able to place any of its profiles in a proper taxonomy. Phyloarray, as defined here, is a strict, phylogenetic approach that offers an alternative to gene-listing, statistical gene-linkage, and clustering, and produces a biologically meaningful classification of specimens through hierarchical class discovery. It incorporates genes with asynchronous expressions (expression values are above and below normals' range) into the analysis, produces higher interplatform congruity, and resolves interplatform comparability.

Phyloarray, as defined in this application, produces its classification by polarizing gene-expression data values into derived and ancestral states using Applicant's polarity assessment algorithm, UNIPAL (or E-UNIPAL), followed by a phylogenetic analysis of the polarized matrix with the parsimony algorithm, MIX. Class discovery here is defined by shared derived expressions (synapomorphies) that delimit natural groups (clades), while gene linkage is inferred from the parsimonious distribution of polarized expressions among the specimens. Interplatform comparability can be carried out with phyloarray by pooling together multiple polarized datasets produced separately and analyzed as long as they have identical probes; we pooled the polarized matrices of leiomyosarcoma and gastric carcinoma, and the two cancers were separated from each other on the cladogram (FIG. 6), and each type proved to be a natural assemblage (a clade) defined by a set of unique synapomorphies. Interplatform congruity was tested by comparing the lists of synapomorphies produced by the polarity assessment of two independent datasets each representing myometrium and leiomyoma, and found a subset of synapomorphies (46/146, 31%) shared by the two groups of leiomyoma, a higher percentage than was produced by statistical methods (13%), despite a quantitative probes difference between the two datasets (7,000 v. 22,000).

Figure 4:
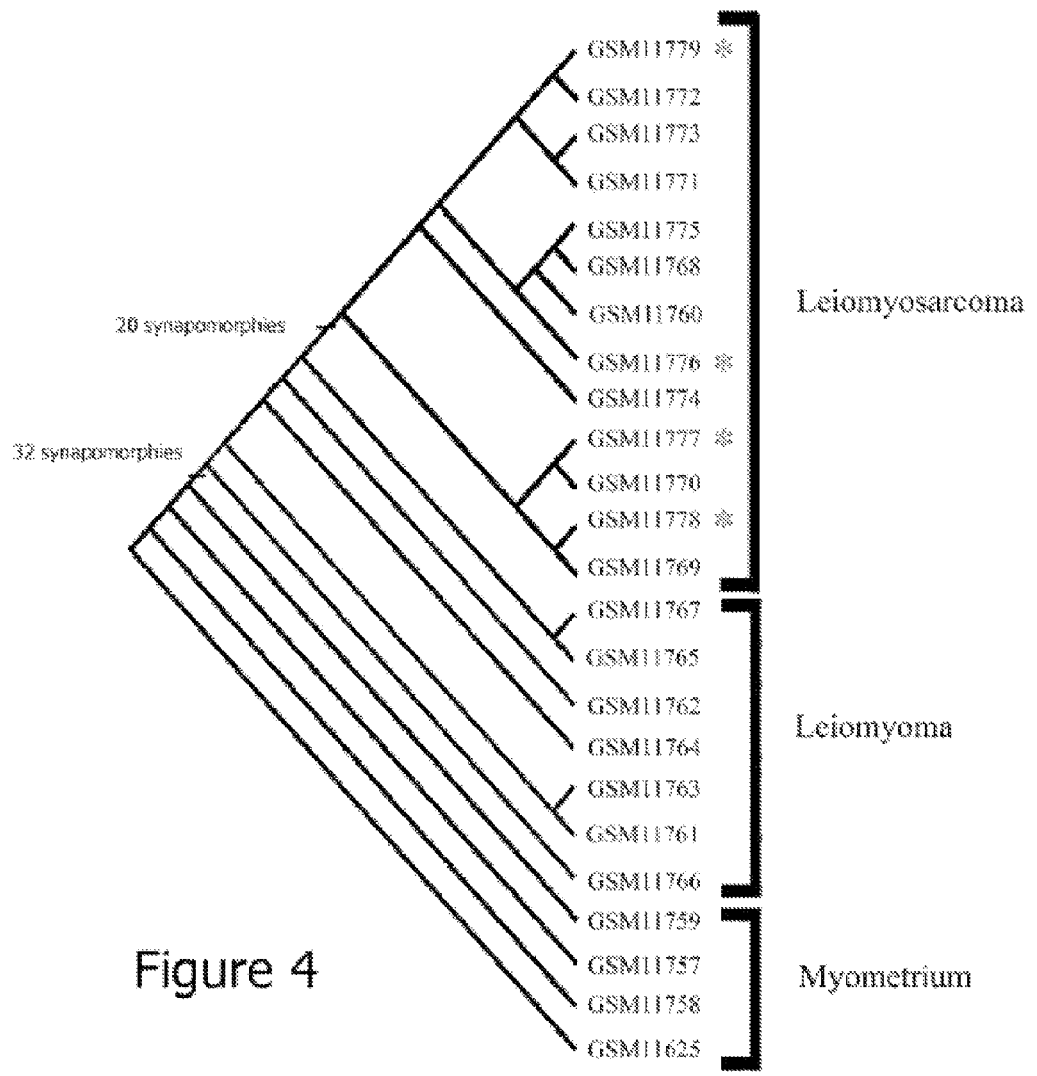
FIG. 4 is a diagrammatic view of a cladogram demonstrating the discriminatory power of the invention in separating cancer (leiomyosarcoma) from benign fibroids (leiomyoma), created using a first set of microarray data and inventive algorithms according to a preferred embodiment of the invention.

Phyloarray is a double-algorithmic approach to the analysis of gene-expression microarray data that offers an alternative to f-test, t-test, and fold-change methods for generating a differentially-expressed gene-list, resolves interplatform comparability problem, produces a higher interplatform congruity, defines biomarkers as synapomorphies, and circumscribes cancer types as clades defined by synapomorphies. It transforms microarray into diagnostic, prognostic, and predictive tool, and provides support for a relationship between uterine fibroids (leiomyoma) and leiomyosarcoma sarcoma (FIG. 4).

Preferred Method and Data Collection

In order to demonstrate the applicability of phylogenetics to microarray gene-expression data, and test the results of interplatform concordance and comparability, three datasets of gene-expression comparative studies, GDS484, GDS533, and GDS1210, were downloaded from NCBI's Gene-Expression Omnibus (www.ncbi.nlm.nih.gov./geo/). The GDS484 was conducted on GPL96 (Affymetrix GeneChip Human Genome U133 Array Set HG-U133A), and the other two studies on GPL80 (Affymetrix GeneChip Human Full Length Array HuGeneFL). The GDS484 was comprised of normal myometrium (n=5) and uterine leiomyomas (n=5) obtained from fibroid afflicted patients. The GDS 533 study encompassed normal myometrium (n=4), benign uterine leiomyoma (n=7), as well as malignant uterine (n=9) and extra-uterine (n=4) leiomyosarcoma specimens. The GDS1210 study included expression profiling of 22 primary advanced gastric cancer tissues and 8 normal specimens.

Polarity Assessment and Phylogenetic Analysis

Our phyloarray does not use comparison of means and folds but rather it converts the continuous values into discontinuous ones through the assessment of each gene value against that of the normals'—a process termed polarity assessment through outgroup comparison to build a matrix of polarized values. Our polarity assessment program, E-UNIPAL, compares independently each gene's value of cancer specimens against those of the outgroup, and scores each as either derived or ancestral, so the matrix of gene-expression values is converted into a matrix of polarized scores.

Example 2

We used all the expression data points of all specimens in the analysis, except those marked as null. For polarity assessment (apomorphic [or derived] vs. plesiomorphic [or ancestral]), data was polarized with a customized algorithm (E-UNIPAL) written by the Applicants that recognized derived values of each gene when compared with the outgroups. Outgroups here are preferably composed of normal specimens only (i.e., those that have been determined to be healthy and/or normal). E-UNIPAL determines the polarity for every data point among the specimens via outgroup comparison, and then scores each value of the study group as derived (1) or ancestral (0). Ideally, the outgroup should be large enough to encompass the maximum variation within normal specimens. In a less preferred, alternate embodiment, the score can be a weighted score (preferably between 1 and 0) that can vary between data points to emphasize or de-emphasize particular values.

The phylogenetic analysis of the present Example, was carried out with MIX, the parsimony program of PHYLIP ver. 3.57c, to produce separate phylogenetic parsimony analyses for each dataset, and the inclusive matrix of the two sets (GDS533 & GDS1210) that included all their specimens. MIX was run in randomized and non-randomized inputs, and no significant differences were observed between the two options.

Phylogenetic trees were drawn using TreeView.

Interplatform Concordance and Comparability

To test interplatform concordance when analyzed phylogenetically, the synapomorphies of the two uterine datasets were compared, GDS484 & GDS533, and recorded the percentage of concordance.

To test interplatform comparability (i.e., whether their datasets can be pooled together for an analysis), we combined the polarized matrices of the two identical platform datasets, GDS533 & GDS1210, processed the combined matrix by MIX, and compared the result to their separate cladograms.

Dichotomously-Expressed Asynchronous Genes

Our analysis identified a specific punctuated pattern of gene expression that seemed to occur only in cancerous specimens where a gene's expression values were around the normals' distribution (over and underexpressed), but did not overlap with it. Lyons-Weiler and his colleagues (2004) also recognized this pattern (through different methods) but did not name it; we termed this pattern dichotomous asynchronicity to reflect its two-tailed distribution.

While F and t-statistics and fold-change may dismiss these asynchronous genes from the gene-list or misrepresent their significance, an outgroup polarity assessment will assess each value as either derived or ancestral and let the parsimony algorithm plot its significance in relation to the rest of the genes. A parsimony phylogenetic algorithm uses the polarity distribution of all genes to produce the most parsimonious classification, one with the lowest number of reversals and parallelisms (multiple origins).

The process of polarity assessment recognized a large number of asynchronous genes that exhibited dichotomous expression (DE). All these genes had their expression values above and below that of the normal specimens, i.e., derived in relation to the outgroups. DE asynchronous genes were found in all the three datasets studied here (Tables 1B-7), and were included within all the analyses.

Cladograms

Parsimony analysis produced one most parsimonious cladogram (having the least number of steps in constructing a classification of specimens) for the uterine GDS 533 dataset (FIG. 4). The topology of the tree showed one large inclusive clade of leiomyomas and leiomyosarcomas delimited by 32 synapomorphies (Table 1B), a terminal clade with 9 sarcoma specimens, middle sarcoma clade with 4 specimens, 5 small basal leiomyoma clades in tandem arrangement followed by 4 basal normal clades.

TABLE 1B

A list of synapomorphies defining a clade composed of all leiomyoma and leiomyosarcoma specimens of GDS533 in comparison with the normal specimens. Synapomorphies include: one OE gene, 8 UE genes, and 23 DE genes.

| | A. Overexpressed synapomorphic genes: | |
|---|---|---|
| D00596 | TYMS thymidylate synthetase | OE(Hoffman, et al., 2004; Quade, et al., 2004) |
| | B. Underexpressed synapomorphic genes: | |
| L19871 | ATF3 activating transcription factor 3 | UE(Hoffman, et al., 2004; Quade, et al., 2004) |
| U62015 | CYR61 cysteine-rich, angiogenic inducer, 61 | UE(Hoffman, et al., 2004; Quade, et al., 2004) |
| X68277 | DUSP1 dual specificity phosphatase 1 | UE(Hoffman, et al., 2004; Quade, et al., 2004) |
| V01512 | FOS v-fos FBJ murine osteosarcoma viral oncogene homolog | UE(Hoffman, et al., 2004), NS(Quade, et al., 2004) |
| L49169 | FOSB FBJ murine osteosarcoma viral oncogene homolog B | NS(Hoffman, et al., 2004), UE(Quade, et al., 2004) |
| J04111 | JUN v-jun sarcoma virus 17 oncogene homolog (avian) | UE(Hoffman, et al., 2004; Quade, et al., 2004) |
| Y00503 | KRT19 keratin 19 | UE(Hoffman, et al., 2004), NS(Quade, et al., 2004) |
| U24488 | TNXB tenascin XB | UE(Hoffman, et al., 2004), UE, OE(Quade, et al., 2004) |
| | C. Dichotomously-expressed synapomorphic genes: | |
| M31994 | ALDH1A1 aldehyde dehydrogenase 1 family, member A1 | UE(Hoffman, et al., 2004), NS(Quade, et al., 2004) |
| X05409 | ALDH2 aldehyde dehydrogenase 2 family (mitochondrial) | NS(Hoffman, et al., 2004; Quade, et al., 2004) |
| D25304 | ARHGEF6 Rac/Cdc42 guanine nucleotide exchange factor (GEF) 6 | NS(Hoffman, et al., 2004; Quade, et al., 2004) |
| K03430 | C1QB complement component 1, q subcomponent, B chain | NS(Hoffman, et al., 2004), OE(Quade, et al., 2004) |
| U60521 | CASP9 caspase 9, apoptosis-related cysteine peptidase | NS(Hoffman, et al., 2004; Quade, et al., 2004) |
| M73720 | CPA3 carboxypeptidase A3 (mast cell) | NS(Hoffman, et al., 2004; Quade, et al., 2004) |
| HG2663-HT2759_at | Cpg-Enriched DNA, Clone S19 (HG3995-HT4265) | NS(Hoffman, et al., 2004; Quade, et al., 2004) |
| M14676 | FYN oncogene related to SRC, FGR, YES | NS(Hoffman, et al., 2004; Quade, et al., 2004) |
| M34677 | F8A1 coagulation factor VIII-associated (intronic transcript) 1 | OE, UE(Quade, et al., 2004) |
| U60061 | FEZ2 fasciculation and elongation protein zeta 2 (zygin II) | NS(Hoffman, et al., 2004; Quade, et al., 2004) |

TABLE 1B-continued

A list of synapomorphies defining a clade composed of all leiomyoma and leiomyosarcoma specimens
of GDS533 in comparison with the normal specimens. Synapomorphies include: one OE gene, 8 UE genes, and 23 DE genes.

| | | |
|---|---|---|
| U86529 | GSTZ1 glutathione transferase zeta 1 (maleylacetoacetate isomerase) | NS(Hoffman, et al., 2004; Quade, et al., 2004) |
| HG358-HT358_at | Homeotic Protein 7, Notch Group (HG358-HT358) | NS(Quade, et al., 2004) |
| AB002365 | KIAA0367 BCH motif-containing molecule at the carboxyl terminal region 1 | NS(Hoffman, et al., 2004), OE, UE(Quade, et al., 2004) |
| U37283 | MFAP5 microfibrillar associated protein 5 | NS(Hoffman, et al., 2004; Quade, et al., 2004) |
| HG406-HT406_at | MFI2 antigen p97 (melanoma associated) identified by monoclonal antibodies 133.2 and 96.5 | NS(Hoffman, et al., 2004; Quade, et al., 2004) |
| M55593 | MMP2 matrix metallopeptidase 2 (gelatinase A, 72 kDa gelatinase, 72 kDa type IV collagenase) | NS(Hoffman, et al., 2004), OE, UE(Quade, et al., 2004) |
| M76732 | MSX1 msh homeobox homolog 1 | NS(Hoffman, et al., 2004; Quade, et al., 2004) |
| L48513 | PON2 paraoxonase 2 | NS(Hoffman, et al., 2004; Quade, et al., 2004) |
| U77594 | RARRES2 retinoic acid receptor responder (tazarotene induced) 2 | NS(Hoffman, et al., 2004; Quade, et al., 2004) |
| M11433 | RBP1 retinol binding protein 1 | NS(Hoffman, et al., 2004; Quade, et al., 2004) |
| L03411 | RDBP RD RNA binding protein | NS(Hoffman, et al., 2004), OE(Quade, et al., 2004) |
| Z29083 | TPBG trophoblast glycoprotein | NS(Hoffman, et al., 2004; Quade, et al., 2004) |
| S73591 | TXNIP thioredoxin interacting protein | NS(Hoffman, et al., 2004; Quade, et al., 2004) |

Last column refers to significant genes list by Hoffman et al. (2004) and Quade et al. (2004),
DE = dichotomously-expressed;
NS = not significant;
OE = overexpressed;
UN = underexpressed.

The cladogram in FIG. 4 shows that the leiomyoma specimens did not form a natural group by themselves—they did not form their own clade separating them from the leiomyosarcomas, and there were no synapomorphies circumscribing them as a clade when the ingroup was composed of leiomyoma and leiomyosarcoma. However, as a paraphyletic group, the leiomyomas shared 146 synapomorphies distinguishing them from the normals (Table 2). The 13 leiomyosarcomas specimens separated into a large terminal clade that was delimited by 20 synapomorphies in comparison with an outgroup composed of leiomyoma and normal specimens (Table 3), and 29 synapomorphies derived in relation to leiomyomas only as an outgroup (Table 4). Extrauterine sarcoma specimens did not assemble together, but rather were scattered within the sarcoma clades (denoted by * on the cladogram in FIG. 4). When the leiomyomas were removed from the comparison, there were 156 synapomorphies delimiting the sarcomas (Table 5).

TABLE 2

A list of synapomorphic genes in leiomyoma specimens of GDS533 in comparison with the normal
specimens. These comprise: 25 OE genes, 42 UE genes, and 79 DE genes.

A. Overexpressed synapomorphic genes:

| | | |
|---|---|---|
| D16469 | ATP6AP1 ATPase, H+ transporting, lysosomal accessory protein 1 | NS(Hoffman, et al., 2004; Quade, et al., 2004) |
| U07139 | CACNB3 calcium channel, voltage-dependent, beta 3 subunit | NS(Hoffman, et al., 2004), OE(Quade, et al., 2004) |
| M11718 | COL5A2 collagen, type V, alpha 2 | NS(Hoffman, et al., 2004; Quade, et al., 2004) |
| U18300 | DDB2 damage-specific DNA binding protein 2, 48 kDa | NS(Hoffman, et al., 2004; Quade, et al., 2004) |
| D38550 | E2F3 E2F transcription factor 3 | NS(Hoffman, et al., 2004; Quade, et al., 2004) |
| M34677 | F8A1 coagulation factor VIII-associated (intronic transcript) 1 | NS(Hoffman, et al., 2004; Quade, et al., 2004) |
| D89289 | FUT8 fucosyltransferase 8 (alpha (1,6) fucosyltransferase) | NS(Hoffman, et al., 2004; Quade, et al., 2004) |
| D86962 | GRB10 growth factor receptor-bound protein 10 | NS(Hoffman, et al., 2004; Quade, et al., 2004) |
| M32053 | H19, imprinted maternally expressed untranslated mRNA | NS(Hoffman, et al., 2004; Quade, et al., 2004) |
| U07664 | HLXB9 homeobox HB9 | OE(Hoffman, et al., 2004; Quade, et al., 2004) |
| D87452 | IHPK1 inositol hexaphosphate kinase 1 | NS(Hoffman, et al., 2004; Quade, et al., 2004) |
| U51336 | ITPK1 inositol 1,3,4-triphosphate 5/6 kinase | NS(Hoffman, et al., 2004; Quade, et al., 2004) |
| AB002365 | KIAA0367 | NS(Hoffman, et al., 2004), OE(Quade, et al., 2004) |
| D78611 | MEST mesoderm specific transcript homolog (mouse) | OE(Hoffman, et al., 2004), NS(Quade, et al., 2004) |
| U19718 | MFAP2 microfibrillar-associated protein 2 | NS(Hoffman, et al., 2004; Quade, et al., 2004) |
| M55593 | MMP2 matrix metallopeptidase 2 (gelatinase A, 72 kDa gelatinase, 72 kDa type IV collagenase) | OE(Hoffman, et al., 2004; Quade, et al., 2004) |
| U79247 | PCDH11X protocadherin 11 X-linked | NS(Hoffman, et al., 2004; Quade, et al., 2004) |
| L24559 | POLA2 polyerase (DNA directed), alpha 2 (70 kD subunit) | NS(Hoffman, et al., 2004; Quade, et al., 2004) |
| M65066 | PRKAR1B protein kinase, cAMP-dependent, regulatory, type I, beta | NS(Hoffman, et al., 2004; Quade, et al., 2004) |
| D14694 | PTDSS1 phosphatidylserine synthase 1 | NS(Hoffman, et al., 2004; Quade, et al., 2004) |
| U24186 | RPA4 replication protein A4, 34 kDa | NS(Hoffman, et al., 2004; Quade, et al., 2004) |

TABLE 2-continued

A list of synapomorphic genes in leiomyoma specimens of GDS533 in comparison with the normal specimens. These comprise: 25 OE genes, 42 UE genes, and 79 DE genes.

| | | |
|---|---|---|
| U85658 | TFAP2C transcription factor AP-2 gamma (activating enhancer binding protein 2 gamma) | NS(Hoffman, et al., 2004; Quade, et al., 2004) |
| D82345 | TMSL8 thymosin-like 8 | NS(Hoffman, et al., 2004; Quade, et al., 2004) |
| D85376 | TRHR thyrotropin-releasing hormone receptor | NS(Hoffman, et al., 2004; Quade, et al., 2004) |
| D00596 | TYMS* thymidylate synthetase | OE(Hoffman, et al., 2004; Quade, et al., 2004) |

B. Underexpressed synapomorphic genes:

| | | |
|---|---|---|
| X03350 | ADH1B alcohol dehydrogenase IB (class I), beta polypeptide | NS(Hoffman, et al., 2004; Quade, et al., 2004) |
| M31994 | ALDH1A1* aldehyde dehydrogenase 1 family, member A1 | UE(Hoffman, et al., 2004), NS(Quade, et al., 2004) |
| X05409 | ALDH2* aldehyde dehydrogenase 2 family (mitochondrial) | NS(Hoffman, et al., 2004; Quade, et al., 2004) |
| L19871 | ATF3* activating transcription factor 3 | UE(Hoffman, et al., 2004; Quade, et al., 2004) |
| U60521 | CASP9 caspase 9, apoptosis-related cysteine peptidase | NS(Hoffman, et al., 2004; Quade, et al., 2004) |
| D49372 | CCL11 chemokine (C—C motif) ligand 11 | NS(Hoffman, et al., 2004; Quade, et al., 2004) |
| X05323 | CD200 molecule | NS(Hoffman, et al., 2004; Quade, et al., 2004) |
| M83667 | CEBPD CCAAT/enhancer binding protein (C/EBP), delta | NS(Hoffman, et al., 2004; Quade, et al., 2004) |
| U90716 | CXADR *coxsackie virus* and adenovirus receptor | NS(Hoffman, et al., 2004; Quade, et al., 2004) |
| M21186 | CYBA cytochrome b-245, alpha polypeptide | NS(Hoffman, et al., 2004; Quade, et al., 2004) |
| U62015 | CYR61* cysteine-rich, angiogenic inducer, 61 | UE(Hoffman, et al., 2004; Quade, et al., 2004) |
| Z22865 | DPT dermatopontin | NS(Hoffman, et al., 2004; Quade, et al., 2004) |
| X56807 | DSC2 desmocollin 2 | NS(Hoffman, et al., 2004; Quade, et al., 2004) |
| X68277 | DUSP1* dual specificity phosphatase 1 | UE(Hoffman, et al., 2004; Quade, et al., 2004) |
| V01512 | FOS* v-fos FBJ murine osteosarcoma viral oncogene homolog | UE(Hoffman, et al., 2004), NS(Quade, et al., 2004) |
| L49169 | FOSB FBJ murine osteosarcoma viral oncogene homolog B | NS(Hoffman, et al., 2004), UE(Quade, et al., 2004) |
| L11238 | GP5 glycoprotein V (platelet) | NS(Hoffman, et al., 2004; Quade, et al., 2004) |
| M36284 | GYPC glycophorin C (Gerbich blood group) | NS(Hoffman, et al., 2004; Quade, et al., 2004) |
| M60750 | HIST1H2BG histone cluster 1, H2bg | NS(Hoffman, et al., 2004; Quade, et al., 2004) |
| X79200 | *Homo spaiens* mRNA for SYT-SSX protein | NS(Hoffman, et al., 2004; Quade, et al., 2004) |
| X92814 | HRASLS3 HRAS-like suppressor 3 | NS(Hoffman, et al., 2004; Quade, et al., 2004) |
| M62831 | IER2 immediate early response 2 | NS(Hoffman, et al., 2004; Quade, et al., 2004) |
| J04111 | JUN* v-jun sarcoma virus 17 oncogene homolog (avian) | UE(Hoffman, et al., 2004; Quade, et al., 2004) |
| Y00503 | KRT19* keratin 19 | NS(Hoffman, et al., 2004; Quade, et al., 2004) |
| X89430 | MECP2 methyl CpG binding protein 2 (Rett syndrome) | NS(Hoffman, et al., 2004; Quade, et al., 2004) |
| U46499 | MGST1 microsomal glutathione S-transferase 1 | NS(Hoffman, et al., 2004; Quade, et al., 2004) |
| M93221 | MRC1 mannose receptor, C type 1 | NS(Hoffman, et al., 2004; Quade, et al., 2004) |
| M76732 | MSX1* msh homeobox homolog 1 (*Drosophila*) | NS(Hoffman, et al., 2004; Quade, et al., 2004) |
| S71824 | NCAM1 neural cell adhesion molecule 1 | OE(Hoffman, et al., 2004), NS(Quade, et al., 2004) |
| X70218 | PPP4C protein phosphatase 4 | NS(Hoffman, et al., 2004; Quade, et al., 2004) |
| U02680 | PTK9 protein tyrosine kinase 9 | NS(Hoffman, et al., 2004; Quade, et al., 2004) |
| U79291 | PTPN11 protein tyrosine phosphatase, non-receptor type 11 (Noonan syndrome 1) | NS(Hoffman, et al., 2004; Quade, et al., 2004) |
| U77594 | RARRES2* retinoic acid receptor responder (tazarotene induced) 2 | NS(Hoffman, et al., 2004; Quade, et al., 2004) |
| M11433, X07438 | RBP1* retinol binding protein 1, cellular | NS(Hoffman, et al., 2004; Quade, et al., 2004) |
| L20859 | SLC20A1 solute carrier family 20 (phosphate transporter), member 1 | NS(Hoffman, et al., 2004; Quade, et al., 2004) |
| M97935 | STAT1 signal transducer and activator of transcription 1, 91 kDa | NS(Hoffman, et al., 2004; Quade, et al., 2004) |
| J04152 | TACSTD2 tumor-associated calcium signal transducer 2 | NS(Hoffman, et al., 2004; Quade, et al., 2004) |
| X14787 | THBS1 thrombospondin 1 | NS(Hoffman, et al., 2004; Quade, et al., 2004) |
| U24488 | TNXB* tenascin XB | UE(Hoffman, et al., 2004; Quade, et al., 2004) |
| Z29083 | TPBG* trophoblast glycoprotein | NS(Hoffman, et al., 2004; Quade, et al., 2004) |
| X51521 | VIL2 villin 2 (ezrin) | UE(Hoffman, et al., 2004), NS(Quade, et al., 2004) |
| D87716 | WDR43 WD repeat domain 43 | NS(Hoffman, et al., 2004; Quade, et al., 2004) |

TABLE 2-continued

A list of synapomorphic genes in leiomyoma specimens of GDS533 in comparison with the normal specimens. These comprise: 25 OE genes, 42 UE genes, and 79 DE genes.

C. Dichotomously-expressed synapomorphic genes

ABCB1; ADRM1; AIM1; ALDH1A3; AMDD; ARHGEF6; ARL4D; ATP5B; Atp8a2; C1QB; CA9; CALM2; CTSB; CCRL2; CD52; CD99; CPA3; DPYD; DSG2; Emx2; FEZ2; FLNA; FOXO1A; FYN; GAPDH; GNB3; GSTZ1; H1F0; H2-ALPHA; HBG2; Ubx, Notch1; Hox5.4; HTR2C; ICA1; IGF2; INSR; ITGA6; ITGA9; KCNK1; KIAA0152; MAP1D; MATK; MBP; MDM4; MFAP5; MFI2 antigen p97; MLH1; MPZ; NDUFS1; NELL2; NNAT; NOS3; NR4A1; OASL; ODC1; OLFM1; PKN2; PON2; PRMT2; PSMC3; PTR2; RANBP2; RBMX; RDBP; RHOG; SAFB2; SCRIB; SELP; SERPINF1; SMS; SPOCK2; ST3GAL1; THRA; TNXB; TTLL4; TXNIP; UPK2; XA; ZNF43

*Also a synapomorphy for leiomyosarcoma.
Last column refers to significant genes list by Hoffman et al. (2004) and Quade et al. (2004),
DE = dichotomously-expressed;
NS = not significant;
OE = overexpressed;
UN = underexpressed.

TABLE 3

A clade composed of all leiomyosarcoma specimens defined by 20 synapomorphies representing genes that are over/under/dichotomously expressed in comparison with the normal and leiomyoma specimens.

A. Overexpressed synapomorphic genes:

| | | |
|---|---|---|
| X54942 | CKS2 CDC28 protein kinase regulatory subunit 2 | NS |
| U68566 | HAX1 HCLS1 associated protein X-1 | NS |
| L03411 | RDBP RD RNA binding protein | OE |
| X59543 | RRM1 ribonucleotide reductase M1 polypeptide | NS |

B. Underexpressed synapomorphic genes:

| | | |
|---|---|---|
| D13639 | CCND2, cyclin D2 | UE |
| D21337 | COL4A6 collagen, type IV, alpha 6 | UE |
| HG2810-HT2921_at | Csh2 chorionic somatomammotropin hormone 2 [*Rattus norvegicus*] | NS |
| L36033 | CXCL12 chemokine (C—X—C motif) ligand 12 (stromal cell-derived factor 1) | NS |
| HG2663-HT2759_at | EMX2 empty spiracles homolog 2 (*Drosophila*). Homeotic Protein Emx2 | NS |
| HG2663-HT2759_at | Homeotic Protein Emx2 | NS |
| HG2810-HT2921_at | HOXA10 homeobox A10 Expressed in the adult human endometrium | UE |
| AB002382 | LOC284394 hypothetical gene supported by NM_001331 | NS |
| U69263 | MATN2 matrilin 2 | UE |
| U85707 | Meis1, myeloid ecotropic viral integration site 1 homolog (mouse) | UE |
| Z29678 | MITF microphthalmia-associated transcription factor | UE |
| L35240 | PDLIM7 PDZ and LIM domain 7 (enigma) | NS |
| D87735 | RPL14 ribosomal protein L14 | NS |
| L14076 | SFRS4 splicing factor, arginine/serine-rich 4 | UE |
| J05243 | SPTAN1 spectrin, alpha, non-erythrocytic 1 (alpha-fodrin) | NS |

C. Dichotomously-expressed synapomorphic gene:

| | | |
|---|---|---|
| M33197 | GAPDH glyceraldehyde-3-phosphate dehydrogenase | NS |

Last column refers to significant genes list by Quade et al. (2004),
DE = dichotomously-expressed;
NS = not significant;
OE = overexpressed;
UN = underexpressed.

TABLE 4

A clade composed of all leiomyosarcoma specimens defined by 29 synapomorphies representing genes that are over/under/dichotomously expressed in comparison with the leiomyoma specimens only.

A. Overexpressed synapomorphic genes:

| | | |
|---|---|---|
| X54941 | CKS1B CDC28 protein kinase regulatory subunit 1B | OE |
| X54942 | CKS2 CDC28 protein kinase regulatory subunit 2 | NS |
| J03060 | GBAP glucosidase, beta; acid, pseudogene | NS |
| U78027 | GLA galactosidase, alpha (associated w/Fabry's) RPL36A ribosomal protein L36a☐No☐4☐4922☐GPX1 glutathione peroxidase 1☐ | NS |
| Y00433 | GPX1 glutathione peroxidase 1 | NS |

TABLE 4-continued

A clade composed of all leiomyosarcoma specimens defined by 29 synapomorphies representing genes that are over/under/dichotomously expressed in comparison with the leiomyoma specimens only.

| | | |
|---|---|---|
| U68566 | HAX1 HCLS1 associated protein X-1 | NS |
| X59543 | RRM1 ribonucleotide reductase M1 polypeptide | NS |
| U12465 | RPL35 ribosomal protein L35 | OE |
| U67674 | SLC10A2 solute carrier family 10 (sodium/bile acid cotransporter family), member 2 | NS |
| | B. Underexpressed synapomorphic: genes | |
| U87223 | CNTNAP1 contactin associated protein 1 | UE☐ |
| D30655 | EIF4A2 eukaryotic translation initiation factor 4A, isoform 2 | UE |
| L20814 | GRIA2 glutamate receptor, ionotropic, AMPA 2 | UE |
| M10051 | INSR insulin receptor☐ | NS |
| D79999 | LOC221181 hypothetical gene supported by NM_006437 | NS |
| D14812 | MORF4L2 mortality factor 4 like 2 | UE |
| L36151 | PIK4CA phosphatidylinositol 4-kinase, catalytic, alpha polypeptide☐ | NS |
| D42108 | PLCL1 phospholipase C-like 1☐ | NS |
| L13434 | Ribosomal protein L41 | NS |
| HG921-HT3995_at | Serine/Threonine Kinase, Receptor 2-2, Alt. Splice 3 | NS |
| D31891 | SETDB1 SET domain, bifurcated 1 | UE |
| AB002318 | Talin2 | NS |
| U53209 | TRA2A transformer-2 alpha | NS |
| D87292 | TST thiosulfate sulfurtransferase (rhodanese) | NS |
| M15990 | YES1 v-yes-1 Yamaguchi sarcoma viral oncogene homolog 1☐ | NS |
| | C. Dichotomously_expressed synapomorphic genes: | |
| U56417 | AGPAT1 1-acylglycerol-3-phosphate O-acyltransferase 1 (lysophosphatidic acid acyltransferase, alpha) | NS |
| M63167 | AKT1 v-akt murine thymoma viral oncogene homolog 1 | NS |
| L27560 | IGFBP5 insulin-like growth factor binding protein 5 | NS |
| U40223 | P2RY4 pyrimidinergic receptor P2Y, G-protein coupled, 4 | NS |
| D76444 | RNF103 ring finger protein 103 | NS |

Last column refers to significant genes list by Quade et al. (2004),
DE = dichotomously-expressed;
NS = not significant;
OE = overexpressed;
UN = underexpressed.

TABLE 5

A clade composed of all leiomyosarcoma specimens is defined in relation to normal specimens. Synapomorphies represent genes that are over/under/dichotomously expressed in comparison with the normal specimens only.

| | A. Overexpressed synapomorphic genes: | |
|---|---|---|
| S78187 | CDC25B cell division cycle 25B | NS |
| U40343 | CDKN2D cyclin-dependent kinase inhibitor 2D (p19, inhibits CDK4) | NS |
| X54942 | CKS2 CDC28 protein kinase regulatory subunit 2 | NS |
| X79353 | GDI1 GDP dissociation inhibitor 1 | NS |
| X14850 | H2AFX H2A histone family, member X | NS |
| U51127 | IRF5 interferon regulatory factor 5 | NS |
| U04209 | MFAP1 microfibrillar-associated protein 1 | NS |
| U43177 | MpV17 mitochondrial inner membrane protein | NS |
| U19796 | MRPL28 mitochondrial ribosomal protein L28 | OE |
| U37690 | POLR2L polymerase (RNA) II (DNA directed) polypeptide L, 7.6 kDa | NS |
| M22960 | PPGB protective protein for beta-galactosidase (galactosialidosis) | NS |
| U09210 | SLC18A3 solute carrier family 18 (vesicular acetylcholine), member 3 | NS |
| M86752 | STIP1 stress-induced-phosphoprotein 1 (Hsp70/Hsp90-organizing protein) | OE |
| M26880 | UBC ubiquitin C | OE |
| U43177 | UCN urocortin | NS |
| | B. Underexpressed synapomorphic genes: | |
| M12963 | ADH1A alcohol dehydrogenase 1A (class I), alpha polypeptide | UE |
| HG3638-HT3849_s_at | Amyloid Beta (A4) Precursor Protein, Alt. Splice 2, A4(751) | NS |
| L28997 | ARL1 ADP-ribosylation factor-like 1 | NS |
| Z49269 | CCL14 chemokine (C—C motif) ligand 14 | UE |
| M92934 | CTGF connective tissue growth factor | UE |
| M74099 | CUTL1 cut-like 1, CCAAT displacement protein (Drosophila) | NS |
| M96859 | DPP6 dipeptidyl-peptidase 6 | UE |
| U94855 | EIF3S5 eukaryotic translation initiation factor 3, subunit 5 epsilon, 47 kDa | NS |

TABLE 5-continued

A clade composed of all leiomyosarcoma specimens is defined in relation to normal specimens. Synapomorphies represent genes that are over/under/dichotomously expressed in comparison with the normal specimens only.

| | | |
|---|---|---|
| L25878 | EPHX1 epoxide hydrolase 1, microsomal (xenobiotic) | NS |
| U60061-U69140 | FFZ2 fasciculation and elongation protein zeta 2 (zygin II) | NS |
| X67491 | GLUDP5 glutamate dehydrogenase pseudogene 5 | NS |
| HG4334-HT4604_s_at | Glycogenin | NS |
| X53296 | IL1RN interleukin 1 receptor antagonist | NS |
| X55740 | NT5E 5'-nucleotidase, ecto (CD73) | UE |
| X78136 | PCBP2 poly(rC) binding protein 2 | UE |
| Z50194 | PHLDA1 pleckstrin homology-like domain, family A, member 1 | NS |
| J02902 | PPP2R1A protein phosphatase 2 (formerly 2A), regulatory subunit A (PR 65), alpha isoform | NS |
| J03805 | PPP2CB protein phosphatase 2, catalytic subunit, beta isoform | NS |
| U25988 | PSG11 pregnancy specific beta-1-glycoprotein 11 | NS |
| M98539 | PTGDS prostaglandin D2 synthase 21 kDa (brain) | UE |
| X54131 | PTPRB protein tyrosine phosphatase, receptor type, B | NS |
| M12174 | RHOB ras homolog gene family, member B | NS |
| HG1879-HT1919 | RHOQ ras homolog gene family, member Q | NS |
| M33493 | TPSB2 tryptase beta 2 | NS |
| L14837 | TJP1 tight junction protein 1 (zona occludens 1) | UE |
| HG3344-HT3521_at | UBE2D1 ubiquitin-conjugating enzyme E2D 1 (UBC4/5 homolog, yeast) | NS |
| X98534 | VASP vasodilator-stimulated phosphoprotein | NS |
| X51630 | WT1 Wilms tumor 1 | UE |
| HG3426-HT3610_s_at | Zinc Finger Protein Hzf-16, Kruppel-Like, Alt. Splice 1 | NS |
| M92843 | ZFP36 zinc finger protein 36, C3H type, homolog (mouse) | UE |
| | C. Dichotomously-expressed synapomorphic genes: | |
| U80226 | ABAT 4-aminobutyrate aminotransferase | NS |
| M14758 | ABCB1 ATP-binding cassette, sub-family B (MDR/TAP), member 1 | NS |
| M95178 | ACTN1 actinin, alpha 1 | NS |
| U76421 | ADARB1 adenosine deaminase, RNA-specific, B1 (RED1 homolog rat) | NS |
| U46689 | ALDH3A2 aldehyde dehydrogenase 3 family, member A2 | NS |
| L34820 | ALDH5A1 aldehyde dehydrogenase 5 family, member A1 (succinate-semialdehyde dehydrogenase) | NS |
| M84332 | ARF1 ADP-ribosylation factor 1 | NS |
| D14710 | ATP5A1 ATP synthase, H+ transporting, mitochondrial F1 complex, alpha subunit 1, cardiac muscle | NS |
| X84213 | BAK1 BCL2-antagonist/killer 1 | NS |
| U23070 | BAMBI BMP and activin membrane-bound inhibitor homolog (Xenopus laevis) | NS |
| M33518 | BAT2 HLA-B associated transcript 2 | NS |
| X61123 | BTG1 B-cell translocation gene 1, anti-proliferative | NS |
| S60415 | CACNB2 calcium channel, voltage-dependent, beta 2 subunit | NS |
| M19878 | CALB1 calbindin 1, 28 kDa | NS |
| L76380 | CALCRL calcitonin receptor-like | NS |
| M21121 | CCL5 chemokine (C—C motif) ligand 5 | NS |
| D14664 | CD302 CD302 molecule | NS |
| X72964 | CETN2 centrin, EF-hand protein, 2 | NS |
| U66468 | CGREF1 cell growth regulator with EF-hand domain 1 | NS |
| M63379 | CLU clusterin | NS |
| X52022 | COL6A3 collagen, type VI, alpha 3 | UE |
| L25286 | COL15A1 collagen, type XV, alpha 1 | NS |
| S45630 | CRYAB crystallin, alpha B | NS |
| X95325 | CSDA cold shock domain protein A | NS |
| U03100 | CTNNA1 catenin (cadherin-associated protein), alpha 1, 102 kDa | NS |
| X52142 | CTPS CTP synthase | NS |
| D38549 | CYFIP1 cytoplasmic FMR1 interacting protein 1 | NS |
| X64229 | DEK DEK oncogene (DNA binding) | NS |
| M63391 | DES desmin | UE |
| Z34918 | EIF4G3 eukaryotic translation initiation factor 4 gamma, 3 | NS |
| U97018 | EML1 echinoderm microtubule associated protein like 1 | NS |
| U12255 | FCGRT Fc fragment of IgG, receptor, transporter, alpha | NS |
| U36922 | FOXO1A forkhead box O1A (rhabdomyosarcoma) | NS |
| U91903 | FRZB frizzled-related protein | NS |
| M33197 | GAPDH glyceraldehyde-3-phosphate dehydrogenase | NS |
| U09587 | GARS glycyl-tRNA synthetase | NS |
| U66075 | GATA6 GATA binding protein 6 | NS |
| D13988 | GDI2 GDP dissociation inhibitor 2 | NS |
| U31176 | GFER growth factor, augmenter of liver regeneration (ERV1 homolog, S. cerevisiae) | NS |
| U28811 | GLG1 golgi apparatus protein 1 | NS |
| U66578 | GPR23 G protein-coupled receptor 23 | NS |
| L40027 | GSK3A glycogen synthase kinase 3 alpha | NS |
| U77948 | GTF2I general transcription factor II, i | UE |
| Z29481 | HAAO 3-hydroxyanthranilate 3,4-dioxygenase | NS |

TABLE 5-continued

A clade composed of all leiomyosarcoma specimens is defined in relation to normal specimens. Synapomorphies represent genes that are over/under/dichotomously expressed in comparison with the normal specimens only.

| | | |
|---|---|---|
| D16480 | HADHA hydroxyacyl-Coenzyme A dehydrogenase/3-ketoacyl-Coenzyme A thiolase/enoyl-Coenzyme A hydratase (trifunctional protein), alpha subunit | NS |
| U50079 | HDAC1 histone deacetylase 1 | NS |
| U50078 | HERC1 hect (homologous to the E6-AP (UBE3A) carboxyl terminus) domain and RCC1 (CHC1)-like domain (RLD) 1 | NS |
| M95623 | HMBS hydroxymethylbilane synthase | NS |
| X79536 | HNRPA1 heterogeneous nuclear ribonucleoprotein A1 | NS |
| L15189 | HSPA9B heat shock 70 kDa protein 9B (mortalin-2) | NS |
| U05875 | IFNGR2 interferon gamma receptor 2 (interferon gamma transducer 1) | NS |
| X57025 | IGF1 insulin-like growth factor 1 (somatomedin C) | UE |
| HG3543-HT3739_at | IGF2 insulin-like growth factor 2 (somatomedin A) | NS |
| U40282 | ILK integrin-linked kinase | NS |
| X74295 | ITGA7 integrin, alpha 7 | NS |
| X57206 | ITPKB inositol 1,4,5-trisphosphate 3-kinase B | NS |
| AB002365 | KIAA0367 | UE |
| J00124 | KRT14 keratin 14 (epidermolysis bullosa simplex, Dowling-Meara, Koebner) | NS |
| X05153 | LALBA lactalbumin, alpha- | NS |
| X02152 | LDHA lactate dehydrogenase A | NS |
| HG3527-HT3721_f_at | LHB luteinizing hormone beta polypeptide | NS |
| X86018 | LRRC41 leucine rich repeat containing 41 | NS |
| L38486 | MFAP4 microfibrillar-associated protein 4 | NS |
| D87742 | MIA3 melanoma inhibitory activity family, member 3 | NS |
| M69066 | MSN moesin | NS |
| AB003177 | mRNA for proteasome subunit p27 | NS |
| U47742 | MYST3 MYST histone acetyltransferase (monocytic leukemia) 3 | NS |
| M30269 | NID1 nidogen 1 | NS |
| U80669 | NKX3-1 NK3 transcription factor related, locus 1 (Drosophila) | NS |
| M10901 | NR3C1 nuclear receptor subfamily 3, group C, member 1 (glucocorticoid receptor) | NS |
| M16801 | NR3C2 nuclear receptor subfamily 3, group C, member 2 | NS |
| U52969 | PCP4 Purkinje cell protein 4 | UE |
| J03278 | PDGFRB platelet-derived growth factor receptor, beta polypeptide | NS |
| D37965 | PDGFRL platelet-derived growth factor receptor-like | NS |
| Z49835 | PDIA3 protein disulfide isomerase family A, member 3 | NS |
| U78524 | PIAS1 protein inhibitor of activated STAT, 1 | NS |
| U60644 | PLD3 phospholipase D family, member 3 | NS |
| D11428 | PMP22 peripheral myelin protein 22 | NS |
| U79294 | PPAP2B phosphatidic acid phosphatase type 2B | NS |
| S71018 | PPIC peptidylprolyl isomerase C (cyclophilin C) | NS |
| X07767 | PRKACA protein kinase, cAMP-dependent, catalytic, alpha | NS |
| X83416 | PRNP prion protein (p27-30) | NS |
| M55671 | PROZ protein Z, vitamin K-dependent plasma glycoprotein | NS |
| U72066 | RBBP8 retinoblastoma binding protein 8 | NS |
| L25081 | RHOC ras homolog gene family, member C | NS |
| U40369 | SAT1 spermidine/spermine N1-acetyltransferase 1 | NS |
| M97287 | SATB1 special AT-rich sequence binding protein 1 (binds to nuclear matrix/scaffold-associating DNA's) | NS |
| U83463 | SDCBP syndecan binding protein (syntenin) | NS |
| U28369 | SEMA3B sema domain, immunoglobulin domain (Ig), short basic domain, secreted, (semaphorin) 3B | NS |
| HG3925-HT4195_at | SFTPA2 surfactant, pulmonary-associated protein A2 | NS |
| L31801 | SLC16A1 solute carrier family 16, member 1 (monocarboxylic acid transporter 1) | NS |
| M91463 | SLC2A4 solute carrier family 2 (facilitated glucose transporter), member 4 | NS |
| U66617 | SMARCD1 SWI/SNF related, matrix associated, actin dependent regulator of chromatin, subfamily d, member 1 | NS |
| U50383 | SMYD5 SMYD family member 5 | NS |
| D43636 | SNRK SNF related kinase | NS |
| D87465 | SPOCK2 sparc/osteonectin, cwcv and kazal-like domains proteoglycan (testican) 2 | NS |
| M61199 | SSFA2 sperm specific antigen 2 | NS |
| U15131 | ST5 suppression of tumorigenicity 5 | NS |
| U95006 | STRA13 stimulated by retinoic acid 13 homolog (mouse) | NS |
| M74719 | TCF4 transcription factor 4 | NS |
| X14253 | TDGF1 teratocarcinoma-derived growth factor 1 | NS |
| U52830 | TERT telomerase reverse transcriptase | NS |
| U12471 | THBS1 thrombospondin 1 | NS |
| U16296 | TIAM1 T-cell lymphoma invasion and metastasis 1 | NS |
| L01042 | TMF1 TATA element modulatory factor 1 | NS |
| U03397 | TNFRSF9 tumor necrosis factor receptor superfamily, member 9 | NS |
| X05276 | TPM4 tropomyosin 4 | UE |
| HG4683-HT5108_s_at | TRAF2 TNF receptor-associated factor 2 | NS |

TABLE 5-continued

A clade composed of all leiomyosarcoma specimens is defined in relation to normal specimens. Synapomorphies represent genes that are over/under/dichotomously expressed in comparison with the normal specimens only.

| | | |
|---|---|---|
| U64444 | UFD1L ubiquitin fusion degradation 1 like (yeast) | NS |
| U39318 | UBE2D3 ubiquitin-conjugating enzyme E2D 3 (UBC4/5 homolog, yeast) | NS |
| X59739 | ZFX zinc finger protein, X-linked | NS |

Last column refers to significant genes list by Quade et al. (2004),
NS = not significant;
DE = dichotomously-expressed;
OE = overexpressed;
UN = underexpressed.

Figure 5:
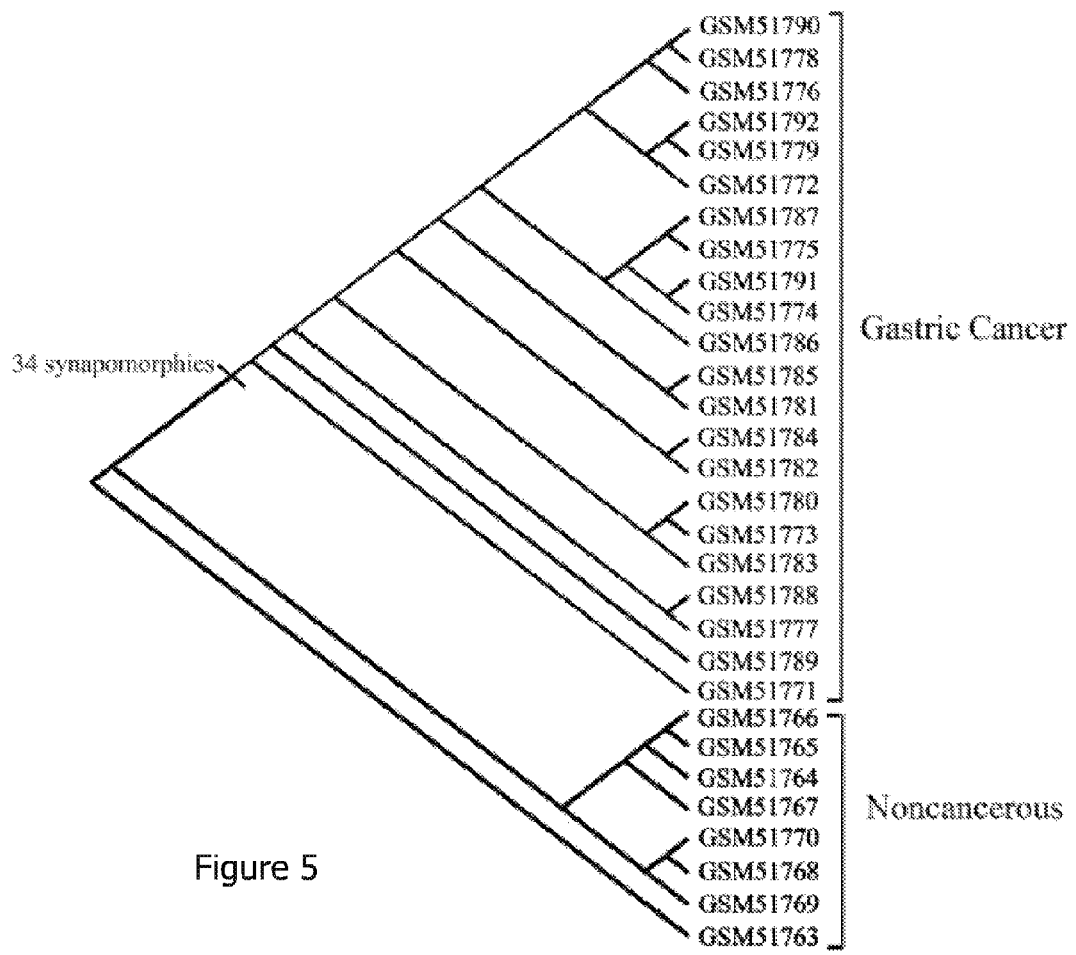
FIG. 5 is a diagrammatic view of a cladogram showing a number of gastric cancer specimens sharing 34 uniquely derived gene expressions (synapomorphies), created using a second set of microarray data and inventive algorithms according to a preferred embodiment of the invention.

For the gastric dataset, GDS1210, parsimony analysis produced one most parsimonious cladogram (FIG. 5). The cladogram topology showed two terminal clades with 6 and 5 specimens respectively and a tandem arrangement of 6 small clades with largest Having 3 specimens. All of the gastric cancer clades formed an inclusive clade that was circumscribed by 34 synapomorphies (Table 6). In a list by list comparison, our 34 synapomorphies for the gastric cancer overlapped only with one common gene (CST4) from the gene list Hippo et al. (2002).

TABLE 6

A list of 34 synapomorphies defining a clade composed of all gastric cancer specimens of GDS1210 dataset. Synapomorphies include: 8 OE genes, 24 UE genes, and 2 DE genes in comparison with the normal specimens.

| | A. Overexpressed synapomorphic genes: | |
|---|---|---|
| X81817 | BAP31 mRNA | No |
| D50914 | BOP1 block of proliferation 1 | No |
| X54667 | CST4: cystatin S MGC71923 | Yes |
| L17131 | HMGA1 high mobility group AT-hook 1 | No |
| D63874 | HMGB1 high-mobility group box 1 | No |
| D26600 | PSMB4 proteasome (prosome, macropain) subunit, beta type, 4 | No |
| U36759 | PTCRA pre T-cell antigen receptor alpha PT-ALPHA, PTA | No |
| X89750 | TGIF TGFB-induced factor (TALE family homeobox) | No |
| | B. Underexpressed synapomorphic genes: | |
| X76342 | ADH7 alcohol dehydrogenase 7 (class IV), mu or sigma polypeptide ADH-4 | No |
| M63962 | ATP4A ATPase, H+/K+ exchanging, alpha polypeptide ATP6A | No |
| M75110 | ATP4B ATPase, H+/K+ exchanging, beta polypeptide ATP6B | No |
| J05401 | CKMT2 creatine kinase, mitochondrial 2 (sarcomeric) | No |
| L38025 | CNTFR ciliary neurotrophic factor receptor | No |
| M61855 | CYP2C9: cytochrome P450, family 2, subfamily C, polypeptide 9 CPC9 | No |
| D63479 | DGKD: diacylglycerol kinase, delta 130 kDa DGKdelta, KIAA0145, dgkd-2 | No |
| X99101 | ESR2 estrogen receptor 2 (ER beta) | No |
| U21931 | FBP1 fructose-1,6-bisphosphatase 1 | No |
| HG3432-HT3618_at | Fibroblast Growth Factor Receptor K-Sam, Alt. Splice 1 | No |
| M31328 | GNB3 guanine nucleotide binding protein (G protein), beta polypeptide 3 | No |
| D42047 | GPD1L glycerol-3-phosphate dehydrogenase 1-like | No |
| M62628 | Human alpha-1 Ig germline C-region membrane-coding region, 3' end | No |
| D29675 | Human inducible nitric oxide synthase gene, promoter and exon 1 | No |
| M63154 | Human intrinsic factor mRNA | No |
| Z29074 | KRT9 keratin 9 (epidermolytic palmoplantar keratoderma) EPPK, K9 | No |
| X05997 | LIPF lipase, gastric | No |
| U50136 | LTC4S leukotriene C4 synthase MGC33147 | No |
| X76223 | MAL: mal, T-cell differentiation protein | No |
| U19948 | PDIA2 protein disulfide isomerase family A, member 2 | No |
| L07592 | PPARD peroxisome proliferative activated receptor, delta | No |
| U57094 | RAB27A, member RAS oncogene family | No |
| AC002077 | SLC38A3 solute carrier family 38, member 3 | No |
| Z29574 | TNFRSF17 tumor necrosis factor receptor superfamily, member 17 | No |

TABLE 6-continued

A list of 34 synapomorphies defining a clade composed of all gastric cancer specimens of GDS1210 dataset. Synapomorphies include: 8 OE genes, 24 UE genes, and 2 DE genes in comparison with the normal specimens.

C. Dichotomously-expressed synapomorphic genes:

| | | |
|---|---|---|
| D00408 | CYP3A7 cytochrome P450, family 3, subfamily A, polypeptide 7 CP37, P450-HFLA | No |
| U29091 | SELENBP1 selenium binding protein 1 | No |

Last column refers to significant genes listed by Hippo et al. (2002).
Yes = listed;
No = not listed.

Interplatform Concordance

Testing of interplatform concordance was carried out by comparing the two lists of synapomorphies of the leiomyomas, GDS484 and GDS533. Out of the roughly 22,000 genes in the GDS484 dataset, phyloarray produced a total of 1485 synapomorphic genes circumscribing the leiomyoma specimens; these were distributed as follows: 427 overexpressed (OE), 587 underexpressed (UE), and 471 dichotomously-expressed (DE). While the leiomyomas of the GDS533 were delimited by 146 synapomorphies (25 OE, 42 UE, & 80 DE, Table 2) out of about 7000 gene probes. A comparison between the two sets of leiomyomas' synapomorphies produced 45 shared ones between the two (Table 7), a 31% concordance in synapomorphies despite the sizable difference in the number of probes between the two datasets, which is still better than the 13% concordance between the gene lists of the two published studies (Hoffman, et al., 2004; Quade, et al., 2004).

TABLE 7

A list of overlapping identical (22) and homologous (23) synapomorphic genes in leiomyoma specimens of GDS484 & GDS533; these include: 9 overexpressed, 24 underexpressed, and 12 dichotomously-expressed.

| GDS533 | GDS484 |
|---|---|
| A. Overexpressed synapomorphic genes a. Identical Synapomorphies | |
| DDB2 | DDB2 |
| FUT8 | FUT8 |
| MEST | MEST |
| TMSL8 | TMSL8 |
| TYMS | TYMS |
| b. Homologous synapomorphies | |
| CACNB3 | CACNA1C |
| COL5A2 | COL4A5 |
| KIAA0367 | KIAA0101 |
| PRKAR1B | PRKACB |
| B. Underexpressed synapomorphic genes a. Identical synapomorphies | |
| ALDH1A1 | ALDH1A1 |
| ALDH2 | ALDH2 |
| ATF3 | ATF3 |
| CEBPD | CEBPD |
| CXADR | CXADR |
| CYR61 | CYR61 |
| DUSP1 | DUSP1 |
| FOS | FOS |
| HRASLS3 | HRASLS3 |
| IER2 | IER2 |
| JUN | JUN |
| KRT19 | KRT19 |
| RARRES2 | RARRES2 |

TABLE 7-continued

A list of overlapping identical (22) and homologous (23) synapomorphic genes in leiomyoma specimens of GDS484 & GDS533; these include: 9 overexpressed, 24 underexpressed, and 12 dichotomously-expressed.

| GDS533 | GDS484 |
|---|---|
| TACSTD2 | TACSTD2 |
| TNXB | TNXB |
| VIL2 | VIL2 |
| b. Homologous synapomorphies | |
| CASP9 | CASP4 |
| CYBA | CYB5R1 |
| FOSB | FOS |
| JUNB | JUN |
| PPP4C | PPP1R10 |
| SLC20A1 | SLC18A2 |
| THBS1 | THBD |
| WDR43 | WDR37 |
| C. Dichotomously-expressed synapomorphic Genes a. Identical synapomorphies | |
| CTSB | CTSB |
| b. Homologous synapomorphies | |
| ARL4D | ARL4C |
| FOXO1A | FOXJ3 |
| GNB3 | GNB1L |
| ITGA6 | ITGA2B |
| ITGA9 | ITGA2B |
| KCNK1 | KCNJ5 |
| MFAP5 | MFAP4 |
| PSMC3 | PSMC2 |
| SELP | SELL |
| TXNIP | TXNDC13 |
| ZNF43 | ZNF259P |

However, a better concordance resulted when comparing the 32 synapomorphies of the leiomyomas and leiomyosarcomas clade (GDS533, Table 1) with the 1485 synapomorphies of the leiomyomas of GDS484 (Table 7); the clades' synapomorphies overlapped as follows: 1/1 OE, 7/8 UE (except FOSB), & 8/23 DE, an 89% concordance within the OE & UE and 35% within the DE.

Furthermore, a lower concordance was obtained when comparing synapomorphies against statistically-generated gene lists. The synapomorphies of leiomyomas (GDS533, Table 2) showed 18% concordance (4/25 OE, 8/42 UE) with the 78 significant genes of Hoffman et al. (2004, GDS 484, gene list produced by fold-change), and 16.5% (5/25 OE, 6/42 UE) with the 146 genes of Quad et al. (2004, GDS 533, gene list produced by F-statistic). This was higher than the concordance between the two gene lists of published uterine studies, 12% (3/25 OE, 5/42 UE). The two studies had no mention of DE genes. Therefore, the present methods appear to produce better interplatform concordance and comparability (also see below).

Interplatform Comparability

Figure 6:
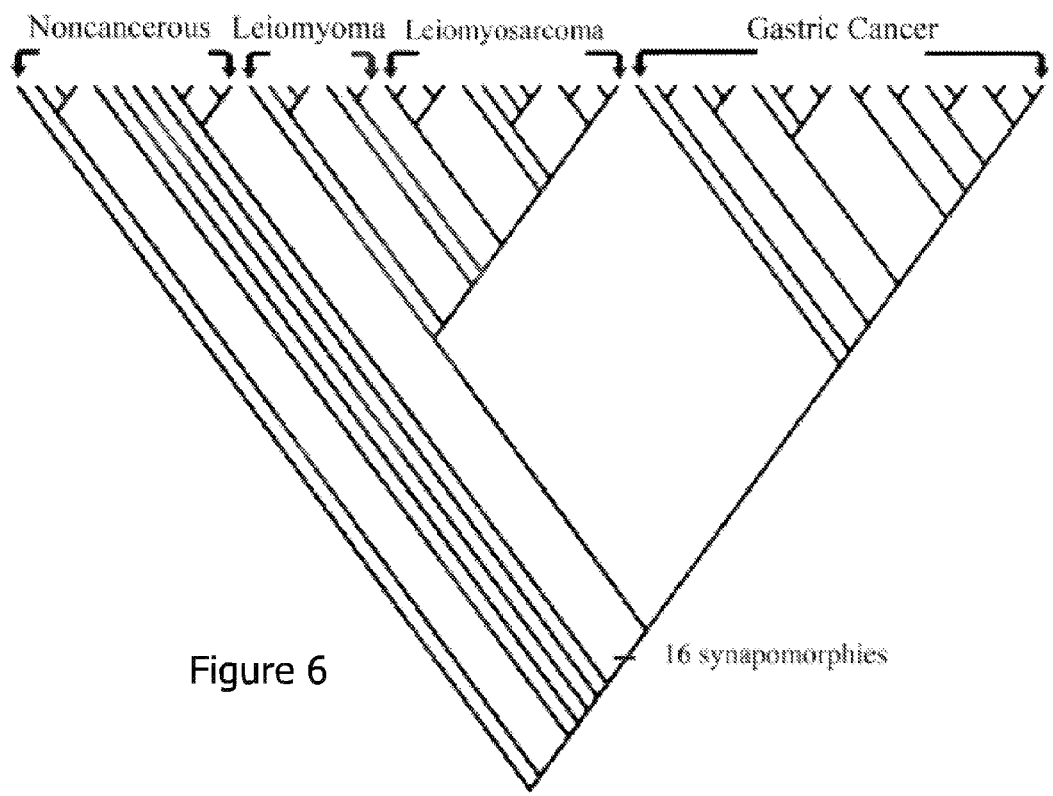
FIG. 6 is a diagrammatic view of a cladogram of showing the discriminatory power of the invention in separating benign specimens from cancerous ones (leiomyosarcoma and gastric), and distinguishing between two types of cancer, created from inclusive data using microarray data and inventive algorithms according to a preferred embodiment of the invention.

Interplatform comparability was carried out on the combined polarized matrices of the gastric (GDS 1210 ) and uterine (GDS 533 ) datasets. Their inclusive parsimony analysis produced one most parsimonious cladogram (FIG. 6). Its topology showed a total separation of the gastric cancer from the uterine leiomyoma and leiomyosarcoma specimens into two large clades.

There were 16 synapomorphies that delimited a clade composed of all the gastric and uterine specimens (Table 8); however, these synapomorphies were non-universal (not derived in all of the specimens of the cancers and leiomyoma).

TABLE 8

A list of 16 non-universal synapomorphies defining a clade composed of all gastric cancer (GDS1210) as well as uterine sarcoma and leiomyoma specimens (GDS533). Genes listed in descending order of the total number of their shared apomorphies.

| ID | Gene | Derived in Gastric (n = 22 specimens) | Derived in Uterine (n = 20 specimens) |
|---|---|---|---|
| Z19083 | TPBG trophoblast glycoprotein | 20 | 20 |
| D21063 | MCM2 minichromosome maintenance deficient 2 | 21 | 18 |
| U51478 | ATP1B3 ATPase, Na+/K+ transporting, beta 3 polypeptide | 21 | 18 |
| X66839 | CA9 carbonic anhydrase IX | 21 | 18 |
| L48513 | PON2 paraoxonase 2 | 19 | 20 |
| X01677-M33197 | GAPDH glyceraldehyde-3-phosphate dehydrogenase [two readings] | 21/18 | 17/19 |
| D87463 | PHYHIP phytanoyl-CoA 2-hydroxylase interacting protein | 19 | 18 |
| X02419 | PLAU plasminogen activator, urokinase | 19 | 18 |
| M60974 | GADD45A growth arrest and DNA-damage-inducible, alpha | 21 | 16 |
| U52830 | *Homo sapiens* Cri-du-chat region mRNA, clone CSC8 | 20 | 17 |
| U52522 | ARFIP2 ADP-ribosylation factor interacting protein 2 (arfaptin 2) | 20 | 16 |
| U25138 | KCNMB1 potassium large conductance calcium-activated channel, subfamily M, beta member 1 | 20 | 16 |
| M25077 | TROVE2 TROVE domain family, member 2 | 20 | 16 |
| U29091 | SELENBP1 selenium binding protein 1 | 22 | 14 |
| X14850 | H2AFX H2A histone family, member X | 19 | 17 |
| L38486 | MFAP4 microfibrillar-associated protein 4 | 16 | 19 |

The resulting comparability cladogram (FIG. 6) showed almost a total agreement with the separate cladograms (FIGS. 4 & 5) indicating a successful pooling of datasets. However, there was a slight variation in the topology of minor branches between the cladograms of FIG. 5 and the inclusive one of FIG. 6. These slight differences are most likely due to the increased number of normal specimens that were used as outgroups in the inclusive cladogram. The outgroups' sizes used here are by no means the most ideal; the larger the membership of the outgroup the more stable the topology of the generated cladogram.

Advantages of the Invention over the Prior Art

Microarray aims to identify differentially expressed genes, and subsequently characterize genetic patterns, classify specimens accordingly, and point out potential biomarkers. Although recent studies have established a high reproducibility of microarray data, most of the problems associated with microarray's analysis arise from using the absolute continuous data values of gene-expression to carry out an analysis, and unrecognizing specific gene-expression patterns such as dichotomous-expression (e.g., where both underexpressed and overexpressed values appear for the same gene in abnormal specimens). This results in discrepancies that affect which genes are considered differentially expressed by the two main ranking criteria for generating gene-lists, the F & t-tests and fold-change.

During our search for a classification model that offers a better predictive significance, as well as congruity with cancer's multiphasic nature and gene-expression asynchronicity, Applicants determined that a phylogenetic parsimony classification of specimens on the basis of gene-expression microarray can be achieved if a computer algorithm produces the polarity assessment for the massive amount of data values of each specimen. Because polarity assessment converts the absolute continuous data values into fixed discontinuous binary states (0/1), our application circumvents the shortcomings of a statistical approach based on F & t-tests or fold-change, statistical gene-linkage, and phenetic clustering calculated from the absolute data values. Additionally, the polarized values (1 for derived and 0 for ancestral) convey an evolutionary significance, since a derived state (1) signifies a state that occurs only in cancerous specimens.

There are several advantages of polarity assessment via outgroup comparison over other methods for the analysis of gene-expression microarray data. It does not set an arbitrary stringency on gene selection especially where the distribution pattern is gene specific (i.e., does not have normal distribution) and the other transformation methods are not optimal for its assessment. Fold-Change and F & t-tests may dismiss from the gene-list those genes with dichotomously asynchronous expressions although they are indicative of a unique expression type and may account for some cancer phenomena such transitional clades, and dichotomous or multi-pathway development in some cancer types. The gene lists of Tables 1C-7C show a large number of DE asynchronous genes that were mostly not considered significant by other methods, or their dichotomous mode was not noticed by the authors of these studies. Polarity assessment recognizes the gene-expression values that are derived in all of the ingroup specimens—it defines synapomorphies, and thus allows us to carry out parsimony phylogenetic analysis and benefit from its unique implications.

For polarity assessment, outgroup size is a very significant factor in correctly identifying synapomorphies, and therefore, delimiting cancerous clades. In the combined analysis (FIG. 6), the increase in outgroup size did not affect the major topology of the cladogram, but rather the internal branching of some clades (normal and gastric cancer) when compared with their single analysis (FIGS. 4 and 5). Because increasing the number of genes in the study does not have the same effect as enlarging the specimen number, it is our conclusion that a successful phyloarray analysis requires a good number of normal specimens to be used as outgroups. For microarray experiments to be meaningful and provide high predictivity, the smallest number of normal specimens that incorporates the maximum variation per population should be established.

Whereas a clustering dendrogram is based on overall gene-linkage of differentially expressed genes, a parsimony cladogram is based on the most parsimonious distribution of derived and ancestral gene-expression values of all genes of all the specimens; it is a map of expression states and profiles among the specimens. The cladogram is described as most parsimonious when it reflects the classification that has the lowest number of parallels and reversals (i.e., homoplasies) to explain the distribution of expression states (ancestral v. derived) among specimens.

Our combined phyloarray analysis of two independently-generated datasets that represent uterine (GDS533) and gastric (GDS1210) cancers confirms that each of these two types of cancer is a natural assemblage of specimens (i.e., a clade) that is circumscribed by a set of synapomorphies. If this can be extended to other types of cancer, then each cancer can be considered a natural clade with its unique gene-expression identifiers—the synapomorphies. There are several implications to this conclusion; the most obvious is its effect on the definition of biomarkers. If a type of cancer is a clade, then any suggested biomarker has to be a proven synapomorphy; otherwise it will not be a universal diagnostic test for all the specimens of this cancer. Some of the currently applied immunohistomarkers are not universal synapomorphies. For example, the memberships of all four clades of the gastric cancers (FIG. 5) did not correlate well with the specimens' immunoreactivity to antibodies against p53, E-cadherin, and β-catenin, and a published two-way clustering did not correlate any better. The discordance between molecular classifications and most of the currently used immunohistomarkers is a problem that can be better addressed in a phylogenetic sense to indicate whether a marker is a synapomorphy or has a random distribution among the subclades of a cancer.

A second implication is that a phylogenetic classification can be a diagnostic tool because it is a process of class discovery based on synapomorphy-defined clades. This can be realized either through a parsimony analysis where the place of a specimen will indicate its pathologic status or by using the synapomorphies as the biomarkers of a specimen, i.e., through class prediction.

A third implication is that the phylogenetic classification is a prognostic tool. Because the cladogram also indicates the direction of change in gene-expression among the specimens by placing those specimens with the advanced number of derived gene-expression patterns at the terminal end of the cladogram (i.e., indicates the direction of cancer progression), and places the specimens with the least number of gene-expression changes at the lower end of the cladogram, it can be used for prognosis and targeted treatment.

Additionally, the phylogenetic classification is a dynamic tool that will incorporate a novel specimen by placing it in the proximity of its sister groups, depending on the number of synapomorphies it shares with other members of a clade, without any radical alteration to the topology of the cladogram.

Interplatform concordance is a criterion that bestows significance on microarray as a valid experimental and clinical platform. Using our phyloarray results, concordance can be tested by comparing the lists of synapomorphies produced by polarity assessment of two or more experiments. We compared the lists of synapomorphies of two independent datasets each representing myometrium and leiomyoma specimens (GDS484 [1485 synapomorphies] & GDS533 [146 synapomorphies, Table 2]), and found 31% concordance in the synapomorphies shared by the two groups of leiomyoma (45/146, Table 7). This was a higher percentage than was produced by statistical methods (13%). Furthermore, we obtained a much higher concordance, 89% within OE & UE and 35% within DE, when comparing the synapomorphies of a clade composed of GDS533 leiomyomas and leiomyosarcomas with the synapomorphies of GDS484 leiomyomas. The concordance between the two studies could have been higher if the number of probes of the GDS533 was closer to GDS484—7,000 v. 22,000.

Interplatform comparability had not been carried out before on microarray data, however, the polarity assessment, which converts the continuous values of gene-expression into discontinuous format that signifies ancestral or derived states, minimizes the noise associated with absolute numbers, and enables us to carry out interplatform comparisons in a phylogenetic sense. Using our phyloarray procedure, interplatform comparability of microarray data can be carried out if each dataset can be polarized separately with E-UNIPAL to produce a polarized matrix. When their probes are identical, two or more polarized sets can be pooled together and analyzed by MIX. As FIG. 6 shows, we have successfully pooled and analyzed two separate polarized datasets (GDS533 & 1210) of gastric cancer as well as uterine leiomyoma and leiomyosarcoma, where the two datasets were prepared separately but on an identical gene chip platform, GPL80.

Our phyloarray analysis of uterine tissues (GDS533) illustrates how a phylogenetic analysis may confront some of the unresolved issues in medicine. One of the persistent questions in pathology is the relationship between leiomyoma and leiomyosarcoma. It has been reported that approximately 1% of leiomyosarcoma may have arisen in pre-existing leiomyoma. By analyzing data of normal uterus, leiomyoma, and leiomyosarcoma, it can be demonstrated that the latter two share a number of synapomorphies and form an inclusive natural clade (Table 1, FIGS. 4 & 6), and that leiomyosarcoma has an additional number of synapomorphies distinguishing them from leiomyoma (Table 3, FIGS. 4 & 6). Although the leiomyoma specimens, when analyzed alone, without the leiomyosarcoma, appear to have a large number of synapomorphies (Table 2), these synapomorphies are not unique to leiomyoma, and the group appears to be paraphyletic (contains some but not all of its members). Leiomyoma as a group does not form a clade within a comprehensive ingroup that includes the leiomyosarcoma; there is not even one gene-expression that is unique to the group itself in this context. Because it shares with the sarcoma its synapomorphies, leiomyoma should be considered an incipient form of leiomyosarcoma.

Conclusion for Phyloarray

Our phyloarray's application to three datasets proves that it provides a successful approach to analyzing and interpreting gene-expression data in a phylogenetic sense. As a double-algorithmic application for carrying out phylogenetic classification of specimens on the basis of their gene-expression microarray data, it offers an alternative to F & t-tests and fold-change methods of generating a differentially-expressed gene-list, brings out a higher interplatform concordance, resolves the interplatform comparability problem, defines biomarkers as synapomorphies, circumscribes cancer types as clades defined by synapomorphies, and transforms microarray into diagnostic, prognostic, and predictive tool. Furthermore, it provided support for a relationship between uterine fibroids and leiomyosarcoma.

3. Metastatic Cancer

Example 3

Figure 7:
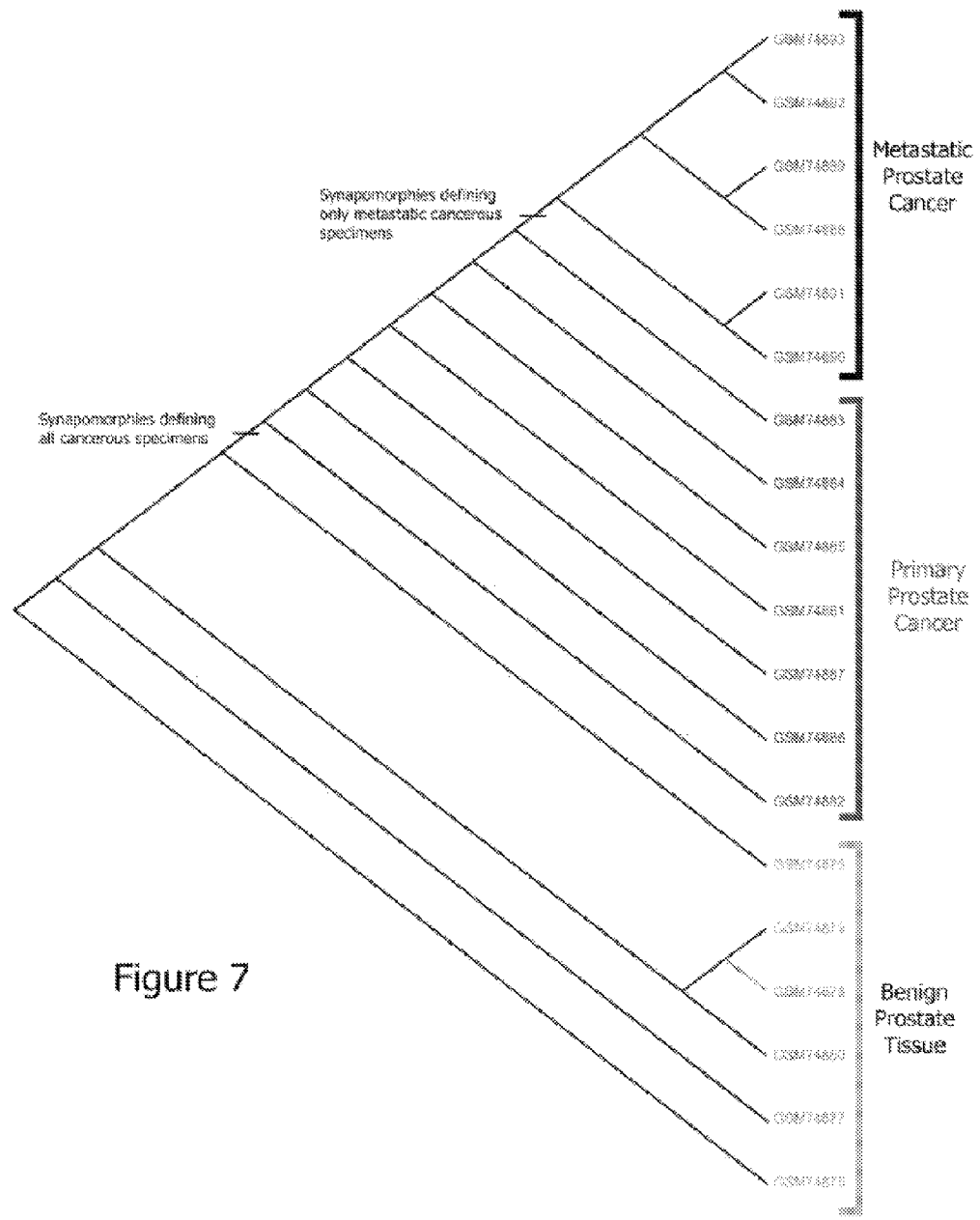
FIG. 7 is a diagrammatic view of a cladogram of showing delineation of primary and metastatic (in red lettering) prostate cancer, according to a preferred embodiment of the invention.

Recent data made available to us has further confirmed the results of the efficacy of the invention. Microarray data on prostate cancer tissues, both primary and metastatic (GDS1439), were obtained from www.nebi.nlm.nih.gov/geo/ and processed according to the invention. FIG. 7 shows a cladogram graphing the results of the primary and metastatic cancer using Applicant's E-UNIPAL algorithm and MIX. Metastatic cancer, which is generally more difficult to treat as the dedifferentiation in the tissue becomes more pronounced, is readily clustered together by the phylogenetic classification. The upper portion of the graph contains the metastatic delineated from the lower portion of the graph containing primary cancer specimens. In particular, the upper part of the cladogram (specimens in red lettering: GSM74890, GSM74891, GSM74888, GSM74889, GSM74892, GSM74893) are the metastatic prostate specimens; the part below it (specimens in black lettering: GSM74882, GSM74886, GSM74887, GSM74881, GSM74885, GSM74884, & GSM74883) are the primary prostate cancers; and the part in green is the normal.

The cladogram shows by Example that 1) the present inventive technique can separate advanced metastatic cancers from primary cancers; 2) it is a proof that the upper part of the cladogram represents the advanced stage of cancer (this point is also illustrated with the cladograms of FIGS. 4 & 6, where the benign leiomyoma [yellow lines] is below the leiomyosarcoma [red lines] that occupies the upper part [distant from normal] of the cladogram)—i.e., the benign leiomyoma is sandwiched between the normal and the cancer); and 3) shows that advanced metastatic cancer has a profile different from primary (have their own shared derived gene expressions), therefore; different biomarkers can be designed for the two conditions.

The upper part of the cladogram (specimens in red lettering: GSM74890, GSM74891, GSM74888, GSM74889, GSM74892, GSM74893) are the metastatic prostate specimens; the part below it (specimens in black lettering: GSM74882, GSM74886, GSM74887, GSM74881, GSM74885, GSM74884, & GSM74883) are the primary prostate cancers; and the part in green is the normal.

While this invention has been described as having a preferred design, it is understood that it is capable of further modifications, uses and/or adaptations of the invention following in general the principle of the invention and including such departures from the present disclosure as come within the known or customary practice in the art to which the invention pertains and as maybe applied to the central features hereinbefore set forth, and fall within the scope of the invention and the limits of the appended claims. It is therefore to be understood that the present invention is not limited to the sole embodiment described above, but encompasses any and all embodiments within the scope of the following claims.

For example, the biomedical applications of our double-algorithmic phylogenetic analytical invention are not limited to cancer assessments, but could be used in all other situations that can be assessed or profiled by the invention, for example, genetic, physiological, and developmental processes where deviation from the normal conditions of the population need to be assessed, profiled, or defined as well as assessing the normal physiological pathways. All genetically-promoted processes that lead to biological reality of functional or causal nature offer a suitable platform for the invention. The following offer some example but not limited to these:

A. The change of a normal stem cell to a specialized cell could be analyzed and key genes and pathways responsible for that shift detected, which might decipher the enigma of cell differentiation and specialization (what makes a bone marrow cell become an immune cell, a muscle progenitor cell become a heart cell, etc . . . ).

B. The developmental processes of a fetus or embryo could be monitored and abnormalities pinpointed. This could help detect at very early stages of pregnancy any debilitating mutations. The amniotic fluid could also be used as a biological specimen, in this case.

C. Similarly, the aging process is also an accumulation of molecular biological events that could be tracked.

D. Medically manageable pathophysiological conditions such as hypertension, diabetes, obesity, cardiovascular problems, arthritis (not limited to only those) could be detected.

E. Health problems caused by environmental or occupational harmful conditions, such as smoking, exposure to toxic chemicals, and warfare could be detected and analyzed.

F. The use of the invention and its resulting synapomorphies will lead to deciphering of cellular and molecular pathways (e.g., signal transduction pathways). The list of a clade's synapomorphies can be used to identify aberrations in the metabolic pathways of the clade's specimens. Synapomorphies affecting pathways are potential therapeutic targets.

We claim:

1. A method of diagnosing a health status of a first specimen of mammalian tissue having a first specimen type by locating a clade corresponding to the first specimen on a cladogram for the specimen type, comprising the steps of:

providing a table of ancestral value ranges for proteins of the specimen type, wherein the ancestral value ranges are defined as the range of one of the group of gene expression values for each gene in an examined range of genes and intensity values of mass spectrometry ("MS") for each protein in an examined wavelength range in a group of healthy specimens of the first specimen type;

providing a cladogram for the specimen type having separate clades corresponding to at least healthy, transitional and unhealthy specimens of the specimen type;

making a polarity assessment by comparing one of the group of gene expression values or mass spectrometry intensity values for the first specimen to the first specimen type ancestral value ranges to determine whether the first specimen values are ancestral values defined as first specimen values within the ancestral value ranges or derived values defined as first specimen values outside the ancestral value ranges;

creating a gene expression array for each gene expression value examined in the examined range of genes, wherein each field in the gene expression array is set to a first range of numbers designating an ancestral value if the corresponding gene expression value is within the ancestral value range and is set to a second range of numbers designating a derived value if the corresponding gene expression value is outside the ancestral value range;

creating an MS intensity value array for each MS intensity value examined in the examined wavelength range, wherein each field in the MS intensity value array is set to a first range of numbers designating an ancestral value if the corresponding MS intensity value is within the ancestral value range and is set to a second range of numbers designating a derived value if the corresponding MS intensity value is outside the ancestral value range at the same wavelength;

using a computer to apply a parsimony phylogenetic algorithm to an array selected from one of the group of the gene expression array and the MS intensity value array to determine a corresponding clade for the first specimen based on only the second range of numbers;

diagnosing the health of the first specimen by determining the closest corresponding clade for the first specimen from the group of clades corresponding to at least healthy, transitional and unhealthy specimens of the specimen type.

2. The method of diagnosing a specimen in claim 1, wherein the step of determining derived values for the first specimen includes using a computer to apply a polarization algorithm to determine at least one of an abnormal derived gene-expression value, abnormal derived protein peak, up regulated protein and down regulated proteins.

3. The method of diagnosing a specimen in claim 1, wherein the step of determining derived values includes determining one of said at least one of an abnormal derived gene-expression value, abnormal derived protein peak, up regulated protein and down regulated proteins.

4. The method of diagnosing a specimen in claim 1, wherein the step of determining derived values for the first specimen includes comparing the specimen to a group of normal specimens of the specimen type having a range of gene-expression values and a range of protein values to determine at least one derived state having at least one of a derived gene-expression value, new derived protein peak, vanished protein peak, and up regulated protein, and down regulated proteins that are outside the gene-expression value range or protein value range of the normal specimens.

5. The method of diagnosing a specimen in claim 1, wherein the step of determining derived values for the first specimen includes the application of a polarity assessment algorithm on mass spectrometry data.

6. The method of diagnosing a specimen in claim 1, wherein the step of determining derived values for the specimen includes polarity assessment of the first specimen's data values including at least one of gene-expression values or mass spectrometry values to a super outgroup of the specimen type's ancestral value ranges to determine at least one of the derived gene-expression values, protein peaks, and up and down regulated proteins outside the range of values in the super outgroup.

7. The method of claim 6, wherein said super outgroup is a hypothetical outgroup that encompasses a data summary of two or more outgroup specimens, and used in their place as an outgroup to run an analysis/diagnosis.

8. The method of diagnosing the first specimen in claim 1, wherein only MS intensity values for the first specimen are examined.

9. The method of diagnosing the first specimen in claim 1, wherein the first range of numbers designating an ancestral value are all equal to zero and wherein the second range of numbers designating a derived value are all equal to 1.

10. The method of diagnosing the first specimen in claim 1, wherein the second range of numbers designating a derived value are all equal to 1.

11. The method of diagnosing the first specimen in claim 1, wherein the second range of numbers designating a derived value does not differentiate between mass spectrometry intensity values for the first specimen higher than the first specimen type ancestral value ranges and a mass spectrometry intensity values for the first specimen lower than the first specimen type ancestral value ranges.

12. The method of diagnosing the first specimen in claim 1, wherein the table of ancestral value ranges comprises a first array of minimum gene expression values in the range of genes or minimum intensity values for proteins in the examined wavelength range and a second array of maximum gene expression values in the range of genes or maximum intensity values for proteins in the examined wavelength range in a group of healthy specimens of the first specimen type.

13. The method of diagnosing the first specimen in claim 1, wherein the unhealthy specimens of the specimen type are cancerous specimens.

14. The method of diagnosing a health status of claim 1, wherein the portion of said cladogram corresponding to healthy specimens indicates the absence of cancer in the specimen, and wherein the portion of said cladogram corresponding to unhealthy specimens indicates the presence of cancer in the specimen.

15. A method of phylogenetically classifying a first specimen comprising the steps of:

performing mass spectrometry (MS) of an outgroup of the specimens consisting essentially of a plurality of non-diseased, healthy, normal specimens of the same type as the first specimen to define an outgroup MS profile for the specimens of the outgroup;

defining an ancestral value range for the outgroup as the range of protein peaks for a range of proteins examined in the plurality of the outgroup specimens MS profiles;

performing mass spectrometry of a plurality of mammalian specimens of known health status and of the same specimen type as the outgroup specimens to determine a MS profile for the mammalian specimens, wherein said mammalian specimens contain at least some specimens afflicted by at least one of the group of cancer, disease, hypertension, diabetes, obesity, cardiovascular problems, arthritis and specimens having pathophysiological conditions;

determining at least one of the group of novel protein peaks, vanished protein peaks, up regulated proteins and down regulated proteins in each of the plurality of mammalian specimens by comparing the mammalian MS profile to the outgroup ancestral value range;

setting each peak or protein value as derived if it is outside of the ancestral value range; and applying a parsimony algorithm to the plurality of mammalian specimens derived values to group the mammalian specimens into a cladogram containing at least some healthy specimens and some unhealthy specimens.

16. The method of claim 15, wherein said outgroup specimens are selected from the group of chimpanzee specimens, non-human primate specimens and primate specimens.

17. The method of claim 16, wherein said mammalian specimens are human specimens.

18. The method of claim 15, wherein said mammalian specimens are human specimens.

19. The method of claim 15, further comprising:

performing mass spectrometry on the first specimen to determine a first specimen MS profile;

determining at least one of the group of novel protein peaks, vanished protein peaks, up regulated proteins and down regulated proteins for the first specimen by comparison of the first specimen MS profile to the ancestral values in computer memory;

using a computer to apply a parsimony algorithm to determine a corresponding clade for the first specimen based on the derived variations of the first specimen from the ancestral value ranges to diagnose the health status of the first specimen.

20. A method of classifying human specimens comprising the steps of:

performing gene-expression of a plurality of outgroup specimens that have been determined to be non-diseased, healthy, or normal;

determining the range of gene-expression values in the plurality of outgroup specimens;

performing gene-expression of a plurality of mammalian specimens;

determining at least one of a group of overexpressed, underexpressed, or dichotomously expressed novel expression values in each of the plurality of mammalian specimens;

applying a parsimony algorithm to the plurality of mammalian specimens to group the mammalian specimens into biologically meaningful classifications containing at least some healthy specimens and some cancerous or unhealthy specimens.

21. The method of delineating unhealthy specimens in claim 20, wherein said outgroup is selected from chimpanzee specimens and primate specimens.

22. A method of phylogenetically classifying the health of a first mammalian specimen comprising the steps of:

performing mass spectrometry (MS) of an outgroup of specimens comprising a plurality of non-diseased, healthy, normal mammalian specimens to define an MS profile for the outgroup specimens;

defining an ancestral value range for the outgroup as the range of protein peaks for the examined range of proteins in the plurality of the outgroup specimens MS profiles;

storing the ancestral value range in a first electronic memory;

performing mass spectrometry of a plurality of mammalian specimens of known health status to determine an MS profile for the mammalian specimens, wherein said mammalian specimens contain at least some specimens afflicted by at least one of the group of cancer, disease, hypertension, diabetes, obesity, cardiovascular problems, and arthritis;

using a computer to determine at least one of the group of novel protein peaks, vanished protein peaks, up regulated proteins and down regulated proteins in each of the plurality of mammalian specimens by computerized comparison of the mammalian MS profile to the outgroup ancestral value range stored in the first electronic memory;

marking each peak or protein value as derived if it is outside of the ancestral value range;

storing the marked derived values for the outgroup in a second electronic memory;

using a computer to apply a parsimony algorithm to the plurality of the mammalian specimens' marked derived values to group the mammalian specimens into a first cladogram;

classifying clades of the first cladogram according to whether the respective clade contains healthy specimens, cancerous or afflicted specimens.

23. A method of diagnosing a health status of a first specimen of mammalian tissue having a first specimen type by mapping a clade corresponding to the first specimen on a cladogram for the specimen type, comprising the steps of:

determining ancestral value ranges for examined proteins of the specimen type, including intensity values of mass spectrometry ("MS") for each examined protein in an examined m-z range in a group of healthy specimens of the first specimen type;

wherein determining the ancestral value ranges includes for each examined m/z in the examined wavelength range:

determining a value for the minimum MS intensity value found in the group of healthy specimens at the examined wavelength for the respective examined protein;

determining a value for the maximum MS intensity value found in the group of healthy specimens at the examined wavelength for the respective protein; and defining the ancestral value ranges as the spread from the minimum MS intensity value to the maximum MS intensity value inclusive for each of the respective examined m/z;

providing a cladogram for the specimen type having separate clades corresponding to at least healthy, transitional and unhealthy specimens of the specimen type;

making a polarity assessment on the first specimen by comparing for each tested m/z the mass spectrometry intensity values of the first specimen to the ancestral value ranges for the specimen type at the same m/z value;

said polarity assessment including defining an MS intensity value of a tested protein as ancestral if it falls within the respective ancestral value range and finding an MS intensity value as derived if it falls outside of the respective ancestral value range;

creating an MS intensity value array for each MS intensity value examined in the examined m/z range, wherein each field in the MS intensity value array is set to a first range of numbers designating an ancestral value and is set to a second range of numbers designating a derived value if the corresponding MS intensity value is derived, wherein no number in the first range of numbers the same as a number in the second range of numbers;

using a computer to apply a parsimony phylogenetic algorithm to the MS intensity value array to map the first specimen within the cladogram;

diagnosing the health of the first specimen from the cladogram from the location of the mapping of the first specimen within the cladogram specimen, wherein the cladogram has clades mapped on the cladogram corresponding to at least healthy, transitional and unhealthy specimens of the specimen type.

* * * * *